United States Patent
Rains, Jr. et al.

(10) Patent No.: US 9,743,488 B2
(45) Date of Patent: Aug. 22, 2017

(54) VISUAL PERCEPTION AND ACUITY DISRUPTION TECHNIQUES AND SYSTEMS

(71) Applicant: ABL IP HOLDING LLC, Conyers, GA (US)

(72) Inventors: Jack C. Rains, Jr., Herndon, VA (US); David P. Ramer, Reston, VA (US); Gregg Irvin, Dayton, OH (US)

(73) Assignee: ABL IP HOLDING LLC, Conyers, GA (US)

( * ) Notice: Subject to any disclaimer, the term of this patent is extended or adjusted under 35 U.S.C. 154(b) by 303 days.

(21) Appl. No.: 14/528,455

(22) Filed: Oct. 30, 2014

(65) Prior Publication Data
US 2015/0061502 A1 Mar. 5, 2015

Related U.S. Application Data

(62) Division of application No. 13/463,571, filed on May 3, 2012, now Pat. No. 8,907,809.

(51) Int. Cl.
*H05B 37/02* (2006.01)
*G08B 15/00* (2006.01)
(Continued)

(52) U.S. Cl.
CPC ......... *H05B 37/0218* (2013.01); *G08B 15/00* (2013.01); *A61F 9/023* (2013.01); *G02C 11/10* (2013.01)

(58) Field of Classification Search
CPC .......... H05B 37/0209–37/0245; H05B 39/041; F21V 23/045; F21V 23/0407–23/0485; G08B 15/00
See application file for complete search history.

(56) References Cited

U.S. PATENT DOCUMENTS 4,336,459 A 6/1982 Fay
5,140,226 A 8/1992 Lepper et al.
(Continued)

FOREIGN PATENT DOCUMENTS

WO WO 2006/131860 A1 12/2006

OTHER PUBLICATIONS

"LED Incapacitator," Wikipedia, the free encyclopedia, pp. 1-3, retrieved Jan. 16, 2009. <http:en.wikipedia.org/wiki/LED Incapacitator>.
(Continued)

*Primary Examiner* — Orlando Bousono
(74) *Attorney, Agent, or Firm* — RatnerPrestia

(57) ABSTRACT

Examples of security lighting routines are tailored to disrupt visual perception and/or acuity so as to significantly reduce the ability of a person or persons, who has breached security, to function within a secured space. A routine triggered in response to a security breach may include a flash at a relatively high intensity, some number of times brighter than normal illumination for the space. Some examples of routines include a warning light and/or a pre-flash light emission such as dim lighting or a flicker, to effectively prepare the person in the space for maximum effectiveness of the flash. Other examples of the routines may also include a post-flash sequence of multiple color light emissions, such as alternating emissions in sequence of pulses of different colors of light using emission and/or off time parameters that vary in an irregular manner.

14 Claims, 10 Drawing Sheets

(51) Int. Cl.
*A61F 9/02* (2006.01)
*G02C 11/00* (2006.01)

(56) References Cited

U.S. PATENT DOCUMENTS

| | | | |
|---|---|---|---|
| 5,161,879 A * | 11/1992 | McDermott | F21L 4/027 |
| | | | 200/60 |
| 5,189,344 A | 2/1993 | Rose | |
| 5,629,984 A | 5/1997 | McManis | |
| 5,831,538 A | 11/1998 | Schena | |
| 5,841,946 A | 11/1998 | Naito et al. | |
| 5,854,520 A | 12/1998 | Buck et al. | |
| 5,898,277 A | 4/1999 | Farnsworth et al. | |
| 6,087,781 A | 7/2000 | Leppelmeier | |
| 6,190,022 B1 | 2/2001 | Tocci et al. | |
| 7,032,397 B1 | 4/2006 | Mueller et al. | |
| 7,180,426 B2 | 2/2007 | Rubtsov | |
| 7,500,763 B2 | 3/2009 | Rubtsov | |
| 7,909,484 B2 | 3/2011 | Rubtsov | |
| 2003/0189825 A1* | 10/2003 | Tauch | B44C 5/005 |
| | | | 362/122 |
| 2004/0056773 A1 | 3/2004 | Zimmerman et al. | |
| 2004/0124183 A1 | 7/2004 | Chung | |
| 2006/0119483 A1* | 6/2006 | Rubtsov | F41H 13/0087 |
| | | | 340/574 |
| 2007/0132575 A1 | 6/2007 | Ellul | |
| 2007/0159347 A1* | 7/2007 | Weitzel | G08B 15/002 |
| | | | 340/691.2 |
| 2008/0013311 A1* | 1/2008 | Rubtsov | F41H 13/0087 |
| | | | 362/231 |
| 2008/0022596 A1 | 1/2008 | Boerger et al. | |
| 2008/0198009 A1 | 8/2008 | Hoeben et al. | |
| 2008/0266121 A1 | 10/2008 | Ellul | |
| 2008/0309914 A1* | 12/2008 | Cantin | G01S 17/10 |
| | | | 356/4.01 |
| 2009/0109051 A1* | 4/2009 | Bodden | G08B 15/002 |
| | | | 340/691.2 |
| 2009/0129782 A1* | 5/2009 | Pederson | H04B 10/1143 |
| | | | 398/135 |
| 2009/0244887 A1* | 10/2009 | Rubtsov | F41H 13/0087 |
| | | | 362/109 |
| 2009/0323321 A1* | 12/2009 | Paolini | H05B 33/086 |
| | | | 362/231 |
| 2010/0081411 A1 | 4/2010 | Montenero | |
| 2010/0109869 A1 | 5/2010 | Marr | |
| 2010/0207777 A1 | 8/2010 | Woodford | |
| 2010/0225502 A1 | 9/2010 | Elsheemy | |
| 2010/0264841 A1 | 10/2010 | Shimizu et al. | |
| 2010/0264842 A1 | 10/2010 | Shimizu et al. | |
| 2010/0271205 A1 | 10/2010 | Saunders et al. | |
| 2010/0277097 A1* | 11/2010 | Maxik | F21S 2/00 |
| | | | 315/294 |
| 2010/0309000 A1 | 12/2010 | Munthe-Kaas et al. | |
| 2011/0053299 A1 | 3/2011 | Shimieu et al. | |
| 2011/0062864 A1 | 3/2011 | Shimizu et al. | |
| 2011/0062888 A1 | 3/2011 | Bondy et al. | |
| 2011/0068951 A1 | 3/2011 | Schwartz et al. | |
| 2011/0115993 A1 | 5/2011 | Liu et al. | |
| 2011/0215725 A1* | 9/2011 | Paolini | H05B 33/086 |
| | | | 315/153 |
| 2012/0044331 A1 | 2/2012 | MacNaughton et al. | |
| 2012/0050856 A1 | 3/2012 | Shintani | |
| 2012/0087115 A1* | 4/2012 | Maxik | F21S 2/00 |
| | | | 362/231 |
| 2012/0183301 A1* | 7/2012 | Pederson | H04B 10/1143 |
| | | | 398/135 |
| 2012/0212138 A1* | 8/2012 | Jungwirth | H05B 33/0824 |
| | | | 315/122 |

OTHER PUBLICATIONS

Entire prosecution history of U.S. Appl. No. 13/463,571, filed May 3, 2012, entitled "Visual Perception and Acuity Disruption Techniques and Systems."

* cited by examiner

VISUAL PERCEPTION AND ACUITY DISRUPTION TECHNIQUES AND SYSTEMS

RELATED APPLICATIONS

This application is a divisional of and claims priority to U.S. application Ser. No. 13/463,571, Filed May 3, 2012 entitled "VISUAL PERCEPTION AND ACUITY DISRUPTION TECHNIQUES AND SYSTEMS", the disclosure of which is entirely incorporated herein by reference.

TECHNICAL FIELD

The present subject matter relates to techniques and equipment to provide light, in response to a breach of security in a protected or secured space, that varies parameters of the light in a manner tailored to disrupt visual perception and/or acuity so as to significantly reduce the ability of a person, who has breached the security, to function within the space.

BACKGROUND

There are many facilities today where it is desirable to have a high level of security. For such a facility, it is desirable to deter intrusion; but if an intrusion occurs, it is desirable to discourage and/or prevent the intruder from completing their nefarious purpose while intruding at the facility. Various alarm systems, for example, trigger sound and/or light alarms intended to indicate detection to the intruder and scare the intruder away. Security systems with associated lighting may be used in various government and private enterprise facilities and even in some private residences.

Flashing light systems or devices have also been proposed that may disorient or disable a person. For example, some proposed systems repeatedly flash a light at intensity, color and/or frequency chosen to induce negative effects on a person in the vicinity. This type of approach has been suggested both for implementation as a handheld device similar to a flashlight and for an implementation as a lighting system using one or more fixtures or lamps installed in the secure facility. The flashing light may temporarily blind the person or persons in the vicinity that have breeched the security. Some flashing light sequences may even induce various uncomfortable effects in the mind or body of any person subjected to the light flashing. Although such lighting may disorient or disable a person, it is non-lethal. The intended target, an intruder at the facility or perpetrator who is the target of the flashlight type device, typically will be unable to complete his or her mission. Yet that person usually will not be permanently harmed by exposure to the light, and other people in the vicinity also should not be permanently harmed by collateral exposure to the light.

However, there is still room for further improvement in these types of security lighting systems. For example, with a handheld device, it is necessary for the user to shine the device in the face of the perpetrator, which may not be practical in all situations. If attempted, and unsuccessful, use of such a handheld device may expose the user to an attack by the perpetrator. In a system that uses installed lamps or fixtures as the lighting sources, the impact on the intruder may be reduced if the intruder happens not to be looking at a lamp or fixture at a critical moment in the modulated light sequence. Also, in systems that use a sequence of flashing light to disorient or disable, the algorithms of the light sequencing have been somewhat limited. As a result, a flashing sequence that impacts one person may have little or no effect on another person of different physical, mental or emotional characteristics, e.g. of a different age, of a different physique or having a different optical sensitivity.

BRIEF DESCRIPTION OF THE DRAWINGS

The drawing Figures depict one or more implementations in accord with the present concepts, by way of example only, not by way of limitations. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or circuitry have been described at a relatively high-level, without detail, in order to avoid unnecessarily obscuring aspects of the present teachings.

The various examples described in this section relate to techniques and equipment to provide light, in response to a breach of security in a protected or secured space, in a manner tailored so as to disrupt visual perception and/or acuity in a way that may significantly reduce the ability of the person(s) breaching the security within the space to function. In the examples, the overall routine for emitting various forms of light for security purpose is non-lethal and not likely to cause permanent injury to the person(s) who have breached security or to anyone else who may happen to be within the secured space at the time of the light counter-measure.

Figure 1:
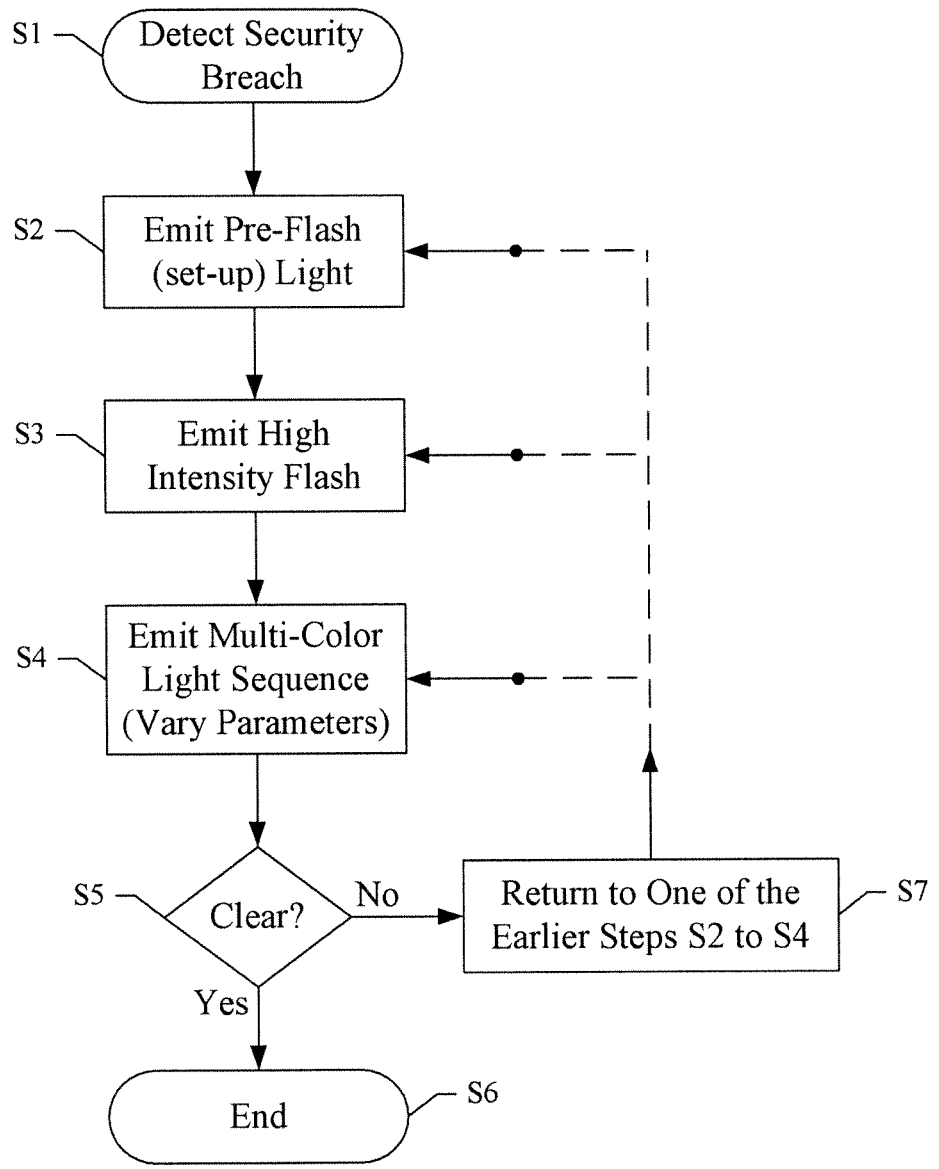
FIG. 1 is a simplified flow chart of a first high-level example of a security lighting procedure.

Reference now is made in detail to the examples illustrated in the accompanying drawings and discussed below. FIG. 1 is a simplified flow chart of a first high-level example of a security lighting procedure. As shown at step S1, the security algorithm for the process begins upon the receipt an input indicative of a breach of security relative to a space protected by the security lighting system (examples discussed later). The input may be a manual input or an input from a device or system providing automatic detection.

The overall security lighting process can rely on a variety of techniques to detect or obtain an indication of a security breach. The breach may or may not be physical or actual. A breach may be a break-in or attack, or it may be any condition that someone might perceive as a potential or actual compromise of security. The security lighting system, or more typically the controller of the system, will have an input for receiving an indication of a breach of security in the protected space. The indication of the breach maybe a signal or other input provided by an automatic detection mechanism, a manual input, or any other appropriate input device. If automatic, the logic for the breach detection may be implemented by a separate system, or the logic for the breach detection may be implemented by the controller of the security lighting system. It may be helpful to consider a couple of examples.

In one example, the system may use a combination of an occupancy sensor and a code-entry keypad. Normally, an occupancy sensor turns lighting in the secured space ON and OFF depending on whether or not someone is in the space. In the secured mode, for example, when the space has been unoccupied for some period of time or security is otherwise turned ON, a person that enters the space must enter a passcode via the keypad within a period of time after the initial detection of the person by the occupancy sensor. Successful entry of the passcode is interpreted as occupancy by an authorized person. Failure to enter the correct passcode within the set time period, however, is interpreted as a breach of security. Although alarms maybe triggered, for purposes of our discussion, the detection of the security breach triggers the security lighting routine.

Clearing of the breach, as detected in a later step in the process, may be detected in several different ways to terminate the security lighting routine. In our first example of breach detection, the breach may be cleared when the occupancy sensor detects that the room is no longer occupied for some period of time, or the system may detect that the breach is cleared upon successful entry of the passcode.

Another approach to detecting a security breach, in the same or a different secured space, would utilize a switch as a trigger for manual activation in the space by authorized personnel. A teller in a branch bank, for example, would activate the switch for an alarm when there is an attempt to rob the bank. In such an example, activation of the switch might trigger a silent alarm report to the police; but for our purposes, activation of the switch would trigger the security lighting routine. As another example, a security guard or the like in the space or observing the space on a monitor might have a similar manual switch to trigger the security lighting routine. In the manual trigger examples of breach detection, the teller or other authorized person might clear the breach by a later activation of the switch or by entry of a secure passcode via a keypad.

The protected space is typically illuminated at a full intensity level, which is normal for human occupancy of the space. The lighting equipment for the space will be in a normal mode prior to the indication of the security breach. Depending on the circumstances, the regular lighting equipment may be full ON, ON but partially dimmed or OFF.

In this example, upon receiving the input indicative of a security breach, the lighting system for the space emits a pre-flash light into the space (step S2). The pre-flash light has an optical characteristic to set-up eyes of a person within the space to be susceptible to subsequent bright lighting.

The security lighting system would have control of the normal lighting in the secured space, at least during a breech of security event, to insure no interference with the pre-flash lighting (S2) and subsequent steps of the security lighting routine. If the security lighting system incorporates regular lighting elements and thereby also provides normal illumination in the secured space, the controller of the system would have full control over the element(s) of the system that provide the normal illumination. The entire lighting for the space could be dimmed, flicker, etc. However, if normal lighting is provided by other elements, such as one or more separate lamps or light fixtures, the system would still be coupled into the normal lighting elements in some manner as to enable at least some control of those lighting elements during a security breech.

For example, it may be preferable to cut-off other light sources during the active operation of the security lighting system in response to a breech of security. For that purpose, the controller of the security lighting system may have a connection to a bypass/cut-off switch installed in the power circuit for the other elements that normally illuminate the secured space. When no breech is detected, the controller would leave the switch in the normal bypass configuration to allow power to reach the other lighting elements that normally illuminate the secured space. The other lighting elements could then be turned ON and OFF, dimmed or otherwise controlled in a normal manner. However, during the security lighting operations, if and/or when appropriate within the overall lighting routine, e.g. at or just before the pre-flash lighting in step S2 the controller of the security lighting system may activate the bypass/cut-off switch to interrupt power to the lighting elements that normally illuminate the secured space. In this way, the separate lighting elements in the space can not be left running or activated in a manner that otherwise might compromise effectiveness of the security lighting operations.

Examples of such pre-flash set-up lighting include dim lighting and flicker. Hence, the pre-flash light may be relatively dim lighting, for example a lower level of lighting if the light in the space was full ON prior to the breech. Either alone (e.g. if the lighting was previously OFF) or after dim lighting, the system lighting the space may emit a flicker.

The dimming and/or the flicker as part of step S2 are intended to set-up any person in the space for maximum impact of the flash. If provided, the dim lighting is at an intensity sufficiently lower than the normal full intensity level for the space and for a sufficient period to cause pupils of a person in the space to dilate, essentially making their eyes more open and therefore more susceptible to a subsequent bright light. Dim lighting may be white light or any colored light. The level of the dim lighting may be approximately 50% or less that the normal full intensity level for the space. If provided, the dim lighting may be for some number of seconds.

Flicker may be somewhat brighter, around or even lower in intensity than the level of dim lighting. After dim lighting, the flicker may be in a range of 10 to 50% of the normal full intensity level for the space. If there is not dim lighting first, and the space has recently been illuminated at the normal full intensity level for the space, the flicker intensity will be no higher than the normal intensity. The flicker typically comprises some small number of flashes separated by periods of no or low light emission, over a relatively short time period, such as 2 or 3 flashes within a second or less. The pulse frequency is below a human's optical fusion rate so as to be perceived as flicker rather than as a continuous light emission. The flicker typically is white but may be red or some other color of light.

The flicker has an attractant effect, in that it tends to stimulate a reflex action causing any person within the space to look in the direction of the source of the flickering light, in this case the security system that is about to produce the bright flash of light. It may also cause such a person to temporarily stop blinking, as part of the reflex action to concentrate their view on the flicker source. As a result of the dimming and flicker in our example, any person within the space, including the perpetrator of the security breech, is more likely to be looking in the direction of the security lighting device and is more likely to have open pupils and/or to have momentarily stopping blinking so as to have their eyes open wide to the following flash, increasing the impact of the subsequent flash.

After the pre-flash light emission (i.e. after step S2), to set-up the person(s) in the space who may have caused the breach of security, the exemplary procedure provides a relatively high-intensity flash of light (at step S3). The flash may be provided by a strobe light type of source or provided by any other source capable of emitting light in step S3 at an intensity level at least twice the normal full intensity level for the space, following the pre-flash light emission in S2. The flash intensity may be several times the normal full intensity level; or the flash intensity level may be one, two or more orders of magnitude greater than the normal full intensity level. With the target set-up to maximize the impact of the flash on the subject(s) within the space, the bright flash in step S3 tends to cause temporary flash blindness and/or a persistent after image.

The retina uses certain biological chemicals to carry light responsive information for transport through the optic nerve to the brain. A high intensity light tends to bleach or oversaturate the retina, depleting the information carrying chemicals. While oversaturated, the retina can no longer produce light responsive information for the brain, particularly when subsequently exposed to low light levels. This condition is sometimes referred to as "flash blindness." Substantially bleaching of the retina causes an after image that may persist for some period of time after the flash. Although there may be some associated psychological pain, the effects of flash blindness and the associated after image are non-lethal and are normally temporary.

The flash and/or the pre-flash lighting could repeat, without more lighting steps; however, mere repetition may be somewhat ineffective, for example, because a person in the space quickly learns not to look at the source of the flash. Hence, the exemplary procedure also includes a post-flash sequence of multiple color light emissions (step S4).

Such a step S4 might further involve alternately emitting a sequence of pulses of two or more different colors of light emission interleaved with periods of no emission. Periods of no emission may be with respect to each color (e.g. each respective color is off for some period) and/or with respect to all colors (periods of no emission of any of the involved colors of light). In our example, each "color" in the sequence is a light of a relatively narrow wavelength band, e.g. as might be produced by a substantially mono-chromatic light source such as an LED of a particular color. One, two or more parameters of light emission and/or off time parameters vary in an irregular manner, within each instance of the sequence and between repetitions or subsequent instances of the sequence. The pulse on times, pulse off times, pulse frequencies and/or overall sequence repetition frequency are such that a human will clearly see the different light colors and will often be able to see the off times. As such, the multi-color sequence emissions are configured such that any apparent repetition rate is below a human's visual fusion frequency (the lower frequency at which the human nervous system tends to integrate light variations into a continuous image). In the more detailed examples, parameters of the multi-color emission sequence vary extensively and/or in an irregular manner to disrupt visual perception and/or acuity and thereby may temporarily disorient or disable any person within the space.

Figure 2:
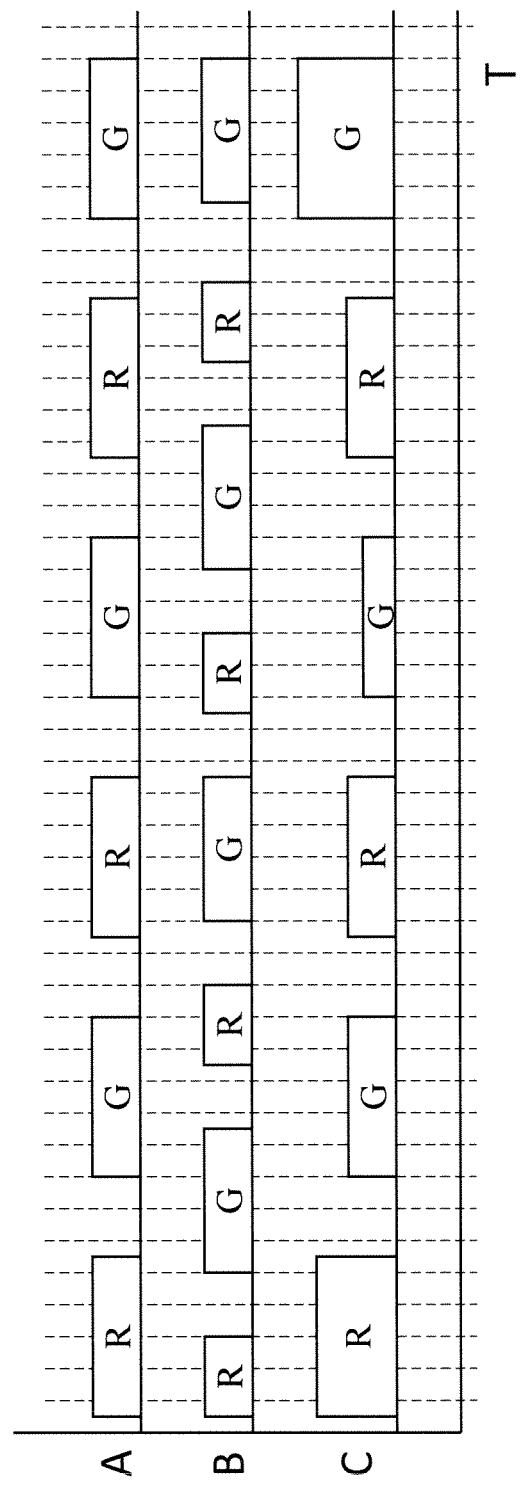
FIG. 2 a pulse diagram useful in explaining the sequence and variables of the sequence in the multi-color light sequence emission step in the procedure of FIG. 1.

In this way, variation(s) in the sequence is configured to potentially disorient or disable a person subject to the sequence of multiple color light emissions for some period of time. FIG. 2 is a pulse diagram showing several examples of a multi-color lighting sequence using two colors of light, such as red (R) and green (G). For simplicity, the drawing shows pulse light emissions of the two colors, R and G; although there may be more colors in the sequence and/or the two or more colors may be different from those shown in this first example.

Human visual processing is sensitive to opponent channels, such as black and white. With respect to color, red and green form one opponent channel, and blue and yellow form another opponent channel. Alternate flashing of colors of such an opponent channel may be disruptive to human optical processing. Red and green tends to be the more effective opponent channel for purposes disrupting visual perception.

Line A of FIG. 2 shows the two color pulse sequence configured to provide fixed: spectral content (always the same two colors), pulse length, amplitude, duty cycle and temporal frequency of each color. In actual implementations, two or more of these parameters of the sequence will vary. Line B of FIG. 2 shows the two color pulse sequence configured to provide fixed spectral content and fixed pulse amplitude. However, in that second example, the different colors have non-equal duty cycles/pulse lengths. Although the off times between pulses and/or the frequencies of the pulses of each color may vary as well, in this example, just the ON-time of the pulse duty cycles vary.

Line C of FIG. 2 shows an example of a two color pulse sequence with variable duty cycles similar to Line B. However, in Line C, the amplitude of light emission also varies form pulse to pulse in the sequence. Hence, in the exemplary sequence of Line C, two parameters (amplitude and pulse on length of duty cycle) of the emission of light of the first color (R) vary pulse to pulse within the illustrated complete repetition of the sequence (the complete line); and the two parameters (amplitude and pulse on length of duty cycle) of the emission of light of the second color (G) vary pulse to pulse within the illustrated complete repetition of the sequence (the complete line). The light emissions in the multi-color sequence may include at least some emissions around or above the normal intensity of lighting for the secured space, although even the highest of these pulse intensities will be lower than the intensity of the flash in step S3.

A complete cycle or instance of the sequence is some set number of emissions of the various light colors. A complete sequence instance may be as few as one emission and one OFF period with respect to each of the included colors. Line A for example, shows three repetitions of a R/OFF/G/OFF sequence; and Line B shows four repetitions of a R/OFF/G/OFF sequence but with differing light ON times as between the R and G ON pulses within each repetition. The example of Line C might represent one instance of a sequence containing six total pulse emissions (three of each color) and interleaved OFF intervals of no light emission of either color. As noted, both light emission duty cycles and amplitudes of light emissions vary from pulse to pulse in the third exemplary sequence.

In each case, the exemplary sequence (Lines A to C) will repeat some number of times within the length of time set for execution of the sequence of multiple color light emissions (step S4 in FIG. 1). In an example like that of Line B, the variable parameter (for instance, duty cycle) with also differ among successive repetitions of the sequence. In a sequence like that of Line C, the two or more variable parameters (e.g. duty cycle and amplitude in the specific example of Line C) will also differ among successive repetitions of the sequence.

The sources used to produce the multi-color light emissions may, as needed, be driven harder than would be typical for normal illumination of the secured space. For example, if LEDs are used to produce the multi-color light emissions, the LEDs may be driven to levels just short of an immediate burn-out intensity. Such over-drive of the LEDs may shorten the performance life of the LEDs to such a degree as to require replacement after the security lighting procedure, but subsequent replacement may be preferable over allowing the intruder to achieve his or her objective and then escape before security personnel can respond.

As noted, a variety of other parameters of the sequence may vary within each repetition of the sequence and/or from repetition to repetition. The variation(s) typically are irregular, in some way, to avoid an observer becoming used to and compensating for a regular repeating pattern of multi-color flashing lights. The variation(s) may be random, for example, resulting in an output sequence where the parameter values are created by chance. Alternatively, the variation(s) may be based on a chaotic function, e.g. based on three linked differential equations at the transition point from orderly to disorderly. Variation of the sequence may be biological, in that it is intended to couple to a known biological function such as temporal frequency in human light level adaptation. Combinations of random, chaotic and biological variations in the sequence may also be used. The irregular variation(s) in the multi-color sequence increase the effectiveness of the sequence in disorienting or disabling a person subject to the security lighting, in that it tends to prevent someone from adapting to the timing of the sequence of emissions.

The impact of the multi-color light sequence in step S4 can be enhanced by appropriately prepared cooperative surfaces in the secured space. One example would be to paint a wall, floor or ceiling in a manner that heightens effectiveness of one or more of the sequence colors. Such an enhancement is "cooperative" in that the paint cooperates with the security lighting system. For example, a phosphor can be added to the wall paint that is normally relatively colorless but is triggered by some of the wavelengths in the security light sequence, e.g. blue, to flash when the security light flashes the particular color. Paints with different such phosphors could be striped to match the illumination colors. If excited by normal illumination, such striping typically is not pleasing in normal operations, i.e. when not used in the secure operation. However, the paint stripes can use phosphors in the paint that are triggered/excited by the different colors of light in the sequence but not triggered by normal lighting. While still pleasing under normal illumination, the stripes alternately flash during the multi-color sequence.

If painted as a color wheel on a surface, e.g. as sections or slices of different color in a circular area of a wall or the like, the alternate flashing of the two or more colors by the security lighting system may make the alternately illuminated painted slices appear to the viewer as a movement of the painted 'wheel.' The painted colors may be actual colors corresponding to those used in the multi-color sequence, or the painted colors may be produced by different phosphors excited by the different emission colors as in the earlier example.

A cooperative surface, for example, may be an otherwise static surface, such as a wall, ceiling or floor in the secured space, or a surface on a critical component in the space, such as a combination lock. Alternatively, the cooperative surface may be automatically introduced into the secured space in response to the security breach that triggered the lighting system. For example, a screen painted with appropriate colors or with appropriate phosphors may be automatically raised from the floor or lowered from the ceiling (much like a projection screen), in response to the initial indication of the security breach. Such a screen could be strategically placed to obscure access to the most sensitive or secure part of the space, e.g. between the main part of the secured space and a wall having the access door to a vault.

Returning to the exemplary procedure of FIG. 1, the sequence of multiple color light emissions (step S4) will continue for some period of time. The set time period in step S5 may be the same period for all passes through the process flow, or the set time period may be a variable parameter that changes each time that the process reaches the branch at step S5. If the breach is cleared within the time period, e.g. if the intruder leaves the secured space, then processing branches at step S5 to step S6 where the security lighting procedure ends. Lighting in the space will return to normal, e.g. to a normal full ON state or possibly to another state of the lighting prior to the breach.

However, at S5, if the breach is not cleared for the set period of time of the multiple color light emissions, then processing branches at step S5 to step S7. Via step S7, the process flow will return to an earlier step in the procedure. In some cycles, the process will keep running the multi-color light sequence of step S4. However, at some point, when the procedure reaches step S5 without clearing of the security breach, the process branches back to on of the even earlier steps, for example, that will at least produce another bright flash. For this purpose processing could flow back to either of steps S2 and S3, which would result in either a flash or a flash proceeded by one or both of the flicker and dim lighting in our examples of pre-flash lighting. The arrows in the drawing that relate to the return are shown in a dotted line manner because there are several ways to implement the return.

The simplest approach would be to set the logic that implements the procedure to always return through S7 to the same one of the prior steps S2 to S4. The process might always return directly to the flash at S3. If the process returns to the pre-flash emission is step S2, the system might be configured to always produce the dim lighting followed by the flicker and then a flash (S3), or the process might always return to step S2 but just produce a flicker followed by the flash (S3). Alternatively, the return path could be another variable parameter of the process so that on different passes through the process flow the process returns to a different one of the prior steps S2 to S4 and/or so as to sometimes light dimly before flicker and other times return to the flicker. The decision as to which prior step to select on each return could be pre-set in the lighting system or could vary in a manner similar to other irregular variations as mentioned earlier.

The security lighting procedures outlined above may be implemented using a variety of different types of device arrangements that incorporate multiple color light sources and one or more flash type light sources. It may be helpful to consider some examples. The examples utilize a configuration in which the flash source is visible even when the system is not flashing and other sources are occluded from direct view. Although not shown, other examples might allow direct illumination from and view of all sources.

Figure 3:
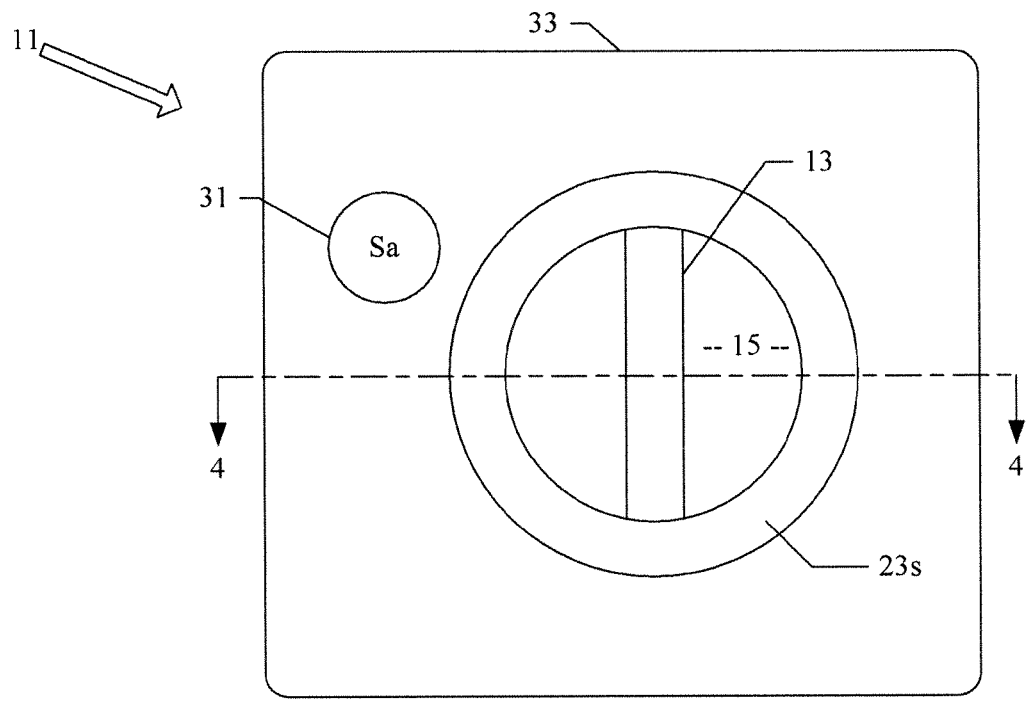
FIG. 3 is a plan view of an example of an implementation of a security lighting system.
Figure 4A:
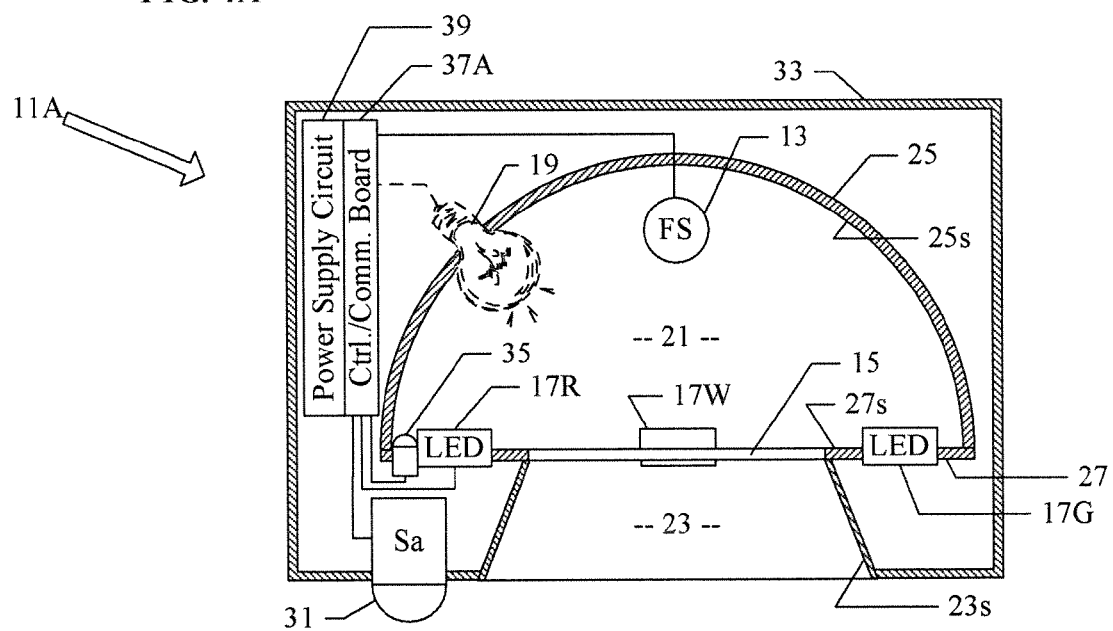
FIG. 4A a cross-sectional view of a first example of the system of FIG. 2, in the form of a light fixture, where the cross section is taken along line 4-4, and in which the fixture includes one or more sources for providing normal lighting in the secured space.
Figure 4B:
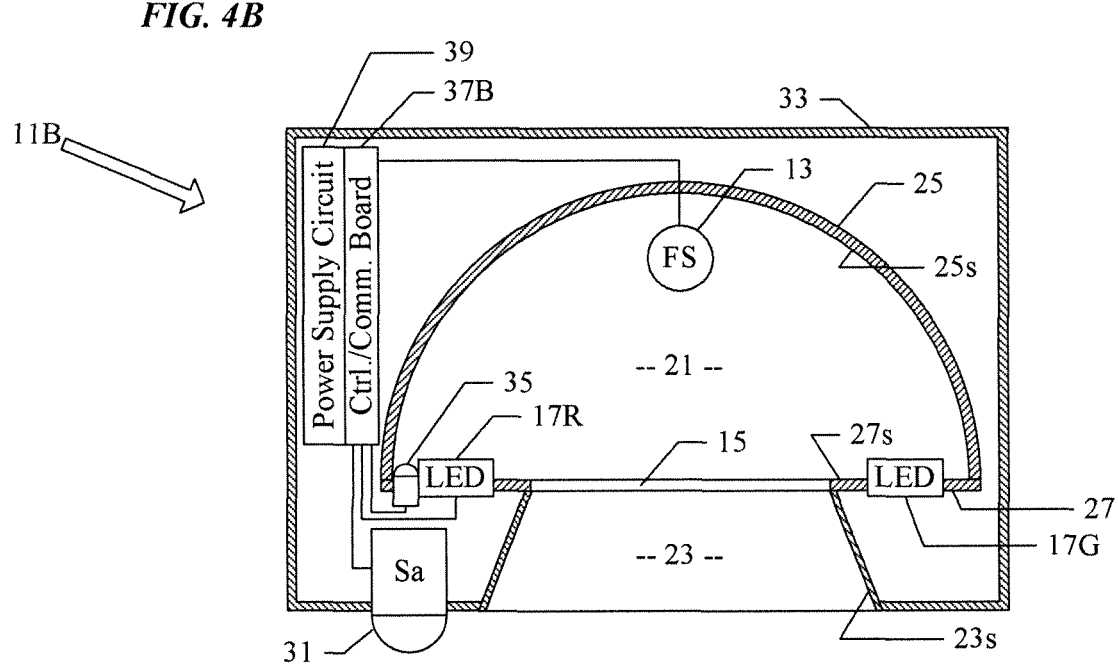
FIG. 4B is a cross-sectional view of an alternate example of the system of FIG. 2 also taken along line 4-4, but implemented as a security lighting module, in which the control in the module connects to and controls an external source of the normal lighting in the secured space.

FIG. 3 is a plan view of an example of an implementation 11 of a security lighting system. The system 11 may take the form of a light fixture that provides normal lighting in addition to the security lighting functions, or the system 11 may take the form of a security module, separate from the normal lighting elements for the secured space. In the later case, the control in the module connects to and controls an external source of the normal lighting in the secured space. To illustrate these points, FIG. 4A is a cross-sectional view of a first example 11A of the system of FIG. 3, in the form of a light fixture that includes one or more sources for providing normal lighting in the secured space. In contrast, FIG. 4B is a cross-sectional view of an alternate example 11B of the system of FIG. 3, in which the control in the module connects to and controls an external source of the normal lighting in the secured space.

The illustrated examples are packaged or configured in a downlight type arrangement. However, the fixture 11A or module 11B may take other forms. The fixture or module may be configured for other orientations. At least the sources, and possibly the system electronics as well, may be implemented in a light bulb for a lamp. The fixture or module may be designed in an obscure or camouflaged manner, so as to not be easily recognized as a security device; or the fixture may be configured in a manner so that when not active it still tends to evoke an emotional reaction that discourages a person for illicit activity.

The security lighting system includes a number of sources. In the illustrated implementations, a number of the sources are not directly visible from outside of the fixture or module. Light from such occluded sources reflects one or more times before emission from the system. The system 11 includes a source (FS) capable of providing the high intensity flash (for use in step S3 in FIG. 1). A variety of different types of sources may be used including solid state devices similar to those found in digital cameras and devices that incorporate such cameras. Such flash sources may be occluded in a manner similar to the other sources in the examples of FIGS. 3 to 4B. However, the illustrated examples utilize a strobe as the source (FS) of the flashes of white light; and the strobe lamp is represented in the examples as a xenon flash tube 13. In the plan view of FIG. 3, a portion of the xenon flash tube 13 is visible through an optically transmissive passage 15. In other implementations, all sources may be arranged for direct emission with relatively little or no internal reflection within the system.

The security lighting system 11 will include at least additional sources for producing the colors of light for the multi-color light sequence. A white light source may also be included. Depending on device output capabilities versus desired output level(s), each source of white or specific color light may include any number of light emitting devices controlled together, controlled in two or more sets of devices or controlled individually.

Although other types of sources of the colors of light may be used, the examples of FIGS. 3 to 4B utilize light emitting diodes (LEDs) of two or more colors as the sources of the multiple colors of light for the sequence (at S4 in FIG. 1). As noted, there may be two, three or more colors of light produced in the sequence, although our specific example utilized two colors red (R) and green (G). Hence, to continue with that example, the exemplary systems of FIGS. 3 to 4B utilize red (R) and green (G) LEDs to produce those colors for the multi-color light sequence. In some procedures, the colored LEDs may be used for dim lighting and/or flicker (S2 in FIG. 1) or for a warning light as in a later exemplary procedure. There may be any appropriate number of each type of LED. In each of FIGS. 4A and 4B, one red LED 17R and one green LED 17G are visible in the cross-sectional views.

Although omitted from the module 11B, the example of a light fixture type implementation 11A also includes one or more elements or sources to enable the fixture 11A to produce white light for normal lighting purposes. The white light could be produced using red LEDs 17R and green LEDs 17G in combination with one or more additional individual color LEDs, such as blue LEDs. Alternatively, the fixture 11A may include one or more additional sources specifically for producing the white light for normal illumination purposes. Such an additional white light source could be any traditional type of light source, as represented generically by the dotted line icon for a light bulb 19. However, in the example of FIG. 4A and the later corresponding circuit example of FIG. 5A, the additional white light source takes the form of one or more white emitting type LEDs 17W, one of which is visible in the cross-sectional view of FIG. 4A. In normal operation, the white LEDs 17W can be driven to produce a desired intensity of white light for a particular degree of illumination, e.g. for the normal full intensity level for the secured space or some reduced percentage thereof for dimmed illumination. If the color characteristic of the white light produced by the white LEDs 17W is not fully satisfactory for a particular application, other light can be added to tune the white light output by the system 11A to a more desirable color characteristic. For example, if the white LEDs 17W produce white light that is somewhat too blue, this can be corrected by adding red light by appropriate operation of one or more of the red LEDs 17R.

In one example, the white source, be it a conventional source 19, white LEDs 17W or a combination of white LEDs with other LED like 17R, is appropriately controlled during the security lighting procedure to produce the pre-flash light at step S2 in the procedure of FIG. 1. For dim lighting, the white light source is turned down to the appropriate level. For a flicker, the white light source is driven in a pulsed ON/OFF manner at an appropriate rate and intensity. In the example of FIGS. 4B and 5B, the pre-flash illumination may be produced using the red LEDs 17R and/or the green LEDs 17G.

Various arrangements of the LEDs, the flash source (FS) together with reflectors and/or other optics may be used to configure the light output for intended security installations and applications. Each of the examples of FIGS. 3 to 4B utilizes a primary optic in the form of a diffusely reflective optical integrating cavity in combination with a secondary optic in the form of a specular or diffusely reflective deflector or concentrator. The cavity is shown at 21 in the cross-sectional view, and the deflector or concentrator is shown at 23.

In both the fixture 11A and the module 11B, although the cavity 21 may take different forms, in the examples, the cavity 21 is formed by a dome 25 and a plate 27. The cavity 21 has a diffusely reflective interior surface 25s and/or 27s and a transmissive optical passage 15. The passage 15 is transmissive with respect to light emitted by the LEDs 17. If an additional or alternative source 19 of white light is provided, the passage 15 would be transmissive with respect to that light as well. The passage 15 may be an actual opening, or the passage 15 may be an optical aperture that is physically closed but allows transmission of light of the appropriate wavelength range from the cavity 21 into the region or area to be illuminated by the device 11A or 11B. For example, the passage 15 may be formed by a transparent or translucent member of portion of the plate 27. Although not shown, the passage 15 may be at other locations and/or there may be additional passages allowing emission in other directions.

The LEDs 17 may be positioned at a variety of different locations and/or oriented in different directions. Various couplings and various light entry locations may be used. In these cavity examples, each LED 17 is coupled to supply light to enter the cavity 21 at a point that directs the light toward a reflective cavity surface so that the LED emissions reflect one or more times inside the cavity 21, and at least one such reflection is a diffuse reflection. As a result, the direct emissions from the source LEDs 17 would not directly pass through the optical output passage 15 of the cavity 21. In examples where the passage 15 is open or transparent, the points of emission into the cavity 21 from the LEDs 17 are not directly observable through the passage 15 from the region illuminated by the output of the security lighting device 11A or 11B. The LEDs 17 therefore are not perceptible as point light sources of high intensity, from the perspective of an area illuminated either of the security lighting devices 11A and 11B.

The cavity 21 may have various shapes. The illustrated cross-section would be substantially the same if the cavity is hemispherical or if the cavity is semi-cylindrical with a lateral cross-section taken perpendicular to the longitudinal axis of the semi-cylinder. For purposes of the discussion, the cavity 21 in the device 11A or 11B is assumed to be hemispherical or nearly hemispherical. In such an example, a hemispherical dome 25 and a substantially flat cover plate or mask 27 form the optical cavity 21. Although shown as separate elements, the dome 25 and plate 29 may be formed as an integral unit. The plate 27 is shown as a flat horizontal member, for convenience, although curved or angled configurations may be used. At least the interior facing surface(s) 25s of the dome 25 is highly diffusely reflective, so that the resulting cavity 21 is highly diffusely reflective with respect to the light energy spectrum produced by the device 11A or 11B. The interior facing surface(s) 27s of the plate 27 is reflective, typically specular or diffusely reflective. In the example, the dome 25 itself is formed of a diffusely reflective material, whereas the plate 27 may be a circuit board or the like on which a coating or layer of reflective material is added or mounted to form the reflective surface 27s.

For efficiency, it is desirable that the diffusely reflective cavity surface(s) have a highly efficient reflective characteristic, e.g. a reflectivity equal to or greater than 90%, with respect to the relevant wavelengths. The entire interior surface (surfaces 25s, 27s of the dome and plate) may be diffusely reflective, or one or more substantial portions may be diffusely reflective while other portion(s) of the cavity surface may have different light reflective characteristics. In some examples, one or more other portions are substantially specular or are semi or quasi specular.

Hence, in each example, the cavity 21 forms an integrating type optical cavity. The transmissive passage or optical aperture 15 allows emission of light generated by the LEDs 17 that has been reflected, diffused and thereby integrated light within the interior of the cavity 21 from the cavity 21 into a region to facilitate at least the security lighting application for the device 11A or 11B. White light from the passage 15, in the fixture 11A, also facilitates general illumination on the secured space, at times when there has not been a security breach. Flash emissions from the source xenon tube 13 also emerge from the cavity through the passage 15. Although shown at approximately the center of the plate 27, the opening or aperture forming transmissive passage 15 may be located elsewhere along the plate or at some appropriate region of the dome 25. In the examples, the passage 15 forms the virtual source of the integrated LED light from the security lighting system device 11A or 11B. When operational, the flash tube 13 will appear as a directly visible source to a person looking toward the aperture 15.

The transmissive passage or optical aperture 15 may serve as the light output if the lighting system 11A or 11B, directing integrated light of relatively uniform intensity distribution and/or flashes of light to a desired area or region to be illuminated in accordance with the general lighting application. It is also contemplated that the security lighting device 11A or 11B may include one or more additional processing elements coupled to the aperture 15, such as a collimator, a grate, lens or diffuser (e.g. a holographic element). In the examples, the system includes a further optical processing element in the form of the deflector or concentrator 23 coupled to the optically transmissive passage 15, to distribute and/or limit the light output to a desired field of illumination.

The deflector or concentrator 23 has a reflective inner surface 23s, to efficiently direct most of the light emerging from the cavity 21 into a relatively narrow field of view. A small opening at a proximal end of the deflector 23 is coupled to the optically transmissive passage 15. The deflector 23 has a larger opening at a distal end thereof. Although other longitudinal cross-sectional shapes may be used, such as various curved reflector shapes (e.g. parabolic or elliptical), the deflector 23 in the examples is conical, essentially in the shape of a truncated cone (straight-sided when shown in cross-section). The angle and/or curvature of the cone wall(s) and the size of the distal opening of the conical deflector 23 define an angular field of light energy emission from the device. Although not shown, the large opening of the deflector 23 may be covered with a transparent plate or lens, or covered with a grating, to prevent entry of dirt or debris through the cone into the system 11A or 11B, and/or to further process the output light energy.

The deflector 23 comprises a reflective interior surface 23s between the distal end and the proximal end. In some examples, at least a substantial portion of the reflective interior surface 23s of the conical deflector 23 exhibits specular reflectivity with respect to the light from the passage 15. However, for some applications, it may be desirable to construct the deflector 23 so that at least some portion(s) of the inner surface 23s exhibit diffuse reflectivity or exhibit a different degree of specular reflectivity (e.g., quasi-secular), so as to tailor the performance of the deflector 23 to a particular lighting application. For other applications, it may also be desirable for the entire interior surface 23s of the deflector 23 to have a diffuse reflective characteristic.

The conical deflector 23 may have a variety of different shapes, depending on the particular lighting application. In the examples, where cavity 21 is hemispherical, the lateral cross-section of the conical deflector 23 (horizontal across the drawing in the illustrated orientation) would typically be circular. Hence, as shown in FIG. 3, the passage and corresponding proximal opening of the deflector 23 as well as the distal opening of the deflector 23 are circular. However, the deflector 23 may be somewhat oval in lateral shape. Although the passage 15 may be round, the distal opening may have other shapes (e.g. oval, rectangular or square); in which case, more curved deflector walls provide a transition from round at the passage coupling to the alternate shape at the distal opening. In applications using a semi-cylindrical cavity, the deflector 23 may be elongated or even rectangular in cross-section. The shape of the aperture 15 also may vary, but will typically match the shape of the small end opening of the deflector 23.

As a practical matter, the size of the cavity 21 is optimized to provide effective integration or combination of light from the desired number of LED type solid state sources 17 and/or the flash source (FS) 13. The size, angle and shape of the deflector 23 determine the area that will be illuminated by the light emitted from the device fixture 11A or the module 11B.

For normal lighting, LEDs typically are driven at levels considered to be sustainable over long periods of time, e.g. that at most cause slow degradation of performance over thousands of hours of LED light output. The white LEDs 17W would be driven in such a manner during normal illumination of the secured space. During a security lighting procedure, in response to a breach of security, the various LEDs 17 can be driven at higher output levels when each is active at appropriate points in the security lighting routine. For many secure installations, it may be preferable to replace the security lighting system 11 due to LED damage caused by such over-driving of the LEDs rather than to allow the intruder to achieve his or her objective and then escape before security personnel can respond.

The security lighting procedure may be adjusted or modulated in some way based on ambient lighting in the secured space. Hence, the examples of FIGS. 3 to 4B include an ambient light sensor (Sa) 31. Sa 31 may be any appropriate device for sensing a characteristic of ambient light in the space. As such, the sensor Sa 31 provides information regarding ambient lighting, at or before the detecting of the input indicative of the breach of security, which may be used to adjust one or more of the parameters of the security lighting procedure. For example, the intensity level of either the dim lighting and/or the flicker can be adjusted based on the sensed intensity of ambient light at or just before detection of the security breach. Flicker frequency or parameters of the multi-color emission sequence are other examples of variables that may be changed in response to detected ambient light conditions.

Each example of the security lighting system (FIGS. 3 to 4B) includes a housing 33, which encloses the sources and the primary and secondary optics. In each of these examples, the sensor Sa 31 is an integral element of the fixture or module; therefore the sensor is attached to receive ambient light through an aperture in a wall of the housing 33. However, for some applications at least, the ambient light sensor Sa 31 could be mounted separate from the housing and connected or wireles sly coupled to the electronics within the fixture 11A or the module 11B.

The initial example of a security lighting procedure (FIG. 1) assumed a pre-flash light emission. This is useful in many circumstances, including situations where there is some illumination in the secured space prior to the security breach. However, there are times in a high security area when there may be little or no ambient light available (e.g., when it is quite dark because lights are OFF and there are no windows into the secured space). In such an instance, the eye is basically already prepped (e.g. dilated). Dim lighting is no longer necessary. The flicker may still improve effectiveness of the flash to attract attention and make the intruder look directly at the device before the first flash. However, even the flicker may be omitted, as the flicker may start to close down the pupils, offsetting any gain due to the attractive effect. Hence, there may be some situations in which the lighting system skips the pre-flash step, e.g. upon an ambient light sensor (Sa) 31 detecting near or total darkness in the secured space at or just before the security breach. When the sensor 31 detects that the secured space is in near or total darkness, the length of down time between flashes or sequences, e.g., where there is no light present may be lengthened to exacerbate the effects.

The fixture 11A or module 11B may also include one or more feedback sensors 35, one of which is visible in each cross-sectional view (FIG. 4A and FIG. 4B). A feedback sensor 35 may be any type of device configured and located around or within the fixture 11A or module 11B so as to detect a condition related to operation of the respective security lighting system for use in controlling lighting by the fixture or module. A security lighting system 11A or 11B may include one or more feedback sensors 35 for sensing operational conditions, such as light source or circuit temperature, light output intensity, or one or more other characteristics of the light produced by the source (e.g. color characteristic), which relate to operation of the lighting system. Such sensors typically provide a local or internal feedback loop at the lighting device system 11A or 11B to enable a processor or other system controller to adjust one or more parameters of operation of the respective system as a function of the sensed operational condition(s). For example, the drive current applied to one or more of the sets of LEDs 17 may be adjusted based on a sensed intensity level so as to achieve a programmed intensity level of a particular output in the overall routine of FIG. 1, e.g. to compensate for degradation of LEDs with extended usage and/or degradation after some period of over-driving.

Whether for ambient detection or feedback, a "sensor" may be as simple as a condition responsive transducer for generating an electrical signal bearing a known relationship to the amount or degree or the like of a particular condition that the transducer detects. However, many implementations utilize sensors that include at least some circuitry for processing the output of the transducer(s) included as part of the sensor. The sensor circuitry receives the signal from the transducer(s) in the sensor and produces an output appropriately formatted for input to the processor or other controller used by the particular system 11.

Each example 11A or 11B of the security lighting system 11 includes various control (Ctrl.) and communication (Comm.) electronics, shown in FIGS. 4A and 4B on a circuit board 37A or 37B. The implementations are generally similar but may differ as to the programming and the driver circuitry, to drive somewhat different types or groups of light sources. At a high level, the electronics on a Ctrl./Comm. circuit board 37A or 37B include a processing device or system, associated driver circuits to operate the light sources in response to signals from the processing device or system and one or more communications elements. The processing device or system could be hard-wired logic or a programmed microprocessor with associated memory devices. Typically, the processing device is a Micro-Control Unit (MCU), which implements the control logic for the security lighting device 11A or 11B, that is to say, controls operations of the respective system 11A or 11B. The MCU may be a microchip device that incorporates a processor serving as the programmable central processing unit (CPU) of the MCU and thus of the lighting system 11A or 11B as well as one or more memories accessible to the CPU. The memory or memories store executable programming for the CPU as well as data for processing by or resulting from processing of the CPU. The MCU may be thought of as a small computer or computer like device formed on a single chip. Such devices are often used as the configurable control elements embedded in special purpose devices rather than in a computer or other general purpose device. More specific examples of the control and communication elements will be discussed later with respect to FIGS. 5A and 5B.

Power for the security lighting system 11A or 11B is provided by a power supply circuit 39, which supplies appropriate voltage(s)/current(s) to the control and communication (Ctrl./Comm.) board 37, which in turn provides appropriate power to various sources 13 and 17 (and possibly 19) of each particular implementation of such a system 11. Although shown separately for convenience, the components of the power supply circuit 39 may be mounted on the same board 37 as the control and communication components, depending on considerations such as board/housing space, heat generation, etc. Typically, the power supply circuit 39 receives electricity from alternating current (AC) mains, although the lighting system 11A or 11B may be driven by a battery or other power source. Also, the security lighting system may have or connect to a back-up battery or other back-up power source to supply power for some period of time in the event of an interruption of power from the AC mains, for example, to prevent an intruder or the like from defeating the system by disconnecting power to the system, to the secured space, or to the entire facility before entering the secured space.

FIG. 3 presented an external view of an exemplary security lighting system 11; and FIGS. 4A and 4B presented cross-sectional views of possible internal arrangements of elements of two examples 11A and 11B of such a system 11. The electrical and functional elements of such systems may be implemented in a variety of ways. To complete the discussion of the specific examples, however, it may be helpful to consider electrical and functional elements of our exemplary fixture 11A and module 11B, as shown in block diagram form in FIGS. 5A and 5B. A number of the electrical elements shown in these two diagrams may be quite similar or the same; and those elements are identified by the same reference numerals in FIGS. 5A and 5B. Where the two circuit examples are substantially the same, both will be described together.

In each circuit example, the fixture 11A or the module 11B includes a set of light sources 41A or 41B. Each set of light sources includes one or more flash sources 13, such as one or more xenon flash tubes. As noted earlier, other types of flash sources may be used, depending on factors like size of the secured space and/or power constraints. In addition, each set of set of light sources 41A or 41B includes sources of two or more colors of light for the multi-color light emission sequence. Although additional sources of additional colors of light may be provided, the examples include two color sources in the form of LED sources of red (R) and green (G) light. Although there may be one LED of each color, in the examples, to provide desired intensity for the security lighting sequence, each set of set of light sources 41A or 41B includes a group of red LEDs 17R as the red light source and a group of green LEDs 17G as the green light source. Similar sets of LEDs but of different colors may be used as sources of additional colors of light in the multi-color light emission sequence.

As noted earlier, the example of a light fixture type implementation 11A also includes one or more elements or sources to enable the fixture 11A to produce white light for normal lighting purposes and in our example for producing white dim lighting and/or white flicker. Although other white light sources may be used, the example of FIG. 5A utilizes an additional set of one or more LEDs 17W, in this case white light LEDs. The module example 11B does not produce the normal illumination in the secured space, and in the example of FIG. 5B does not include the additional white light source.

The module 11B may produce dim lighting and/or flicker using the red LEDs 17R and/or the green LEDs 17G. Although not shown, a security module configuration might include some number of white LEDs for the dim illumination and/or flicker in a manner analogous to the fixture 11A; although typically, the number of white LEDs for such a module would be fewer than in the fixture 11A which produces normal illumination for the secured space.

The fixture 11A controls normal lighting in the secured space by controlling the white LEDs 17W. The module 11B, however, controls other elements, such as one or more separate lamps or light fixtures that provide normal illumination via a bypass/cut-off switch 46. The switch 46 connects into the power circuit (not shown) for the other elements that normally illuminate the secured space. When no breech is detected, the switch is maintained in its normal bypass configuration to allow power to reach the other lighting elements that normally illuminate the secured space. The other lighting elements could then be turned ON and OFF, dimmed or otherwise controlled in a normal manner. During the security lighting operations, if and/or when appropriate, the switch 46 is activated to interrupt power to the lighting elements that normally illuminate the secured space. In this way, the separate lighting elements in the space can not be left running or activated in a manner that otherwise might compromise effectiveness of the security lighting operations. Of course, the module 11B may use other elements and/or strategies to appropriately control the other elements that normally illuminate the secured space. For example, the module may be configured to communicate with and control a dimmer of the other lighting elements so as to more fully integrate control of such element(s) into the security lighting routine.

Figure 5A:
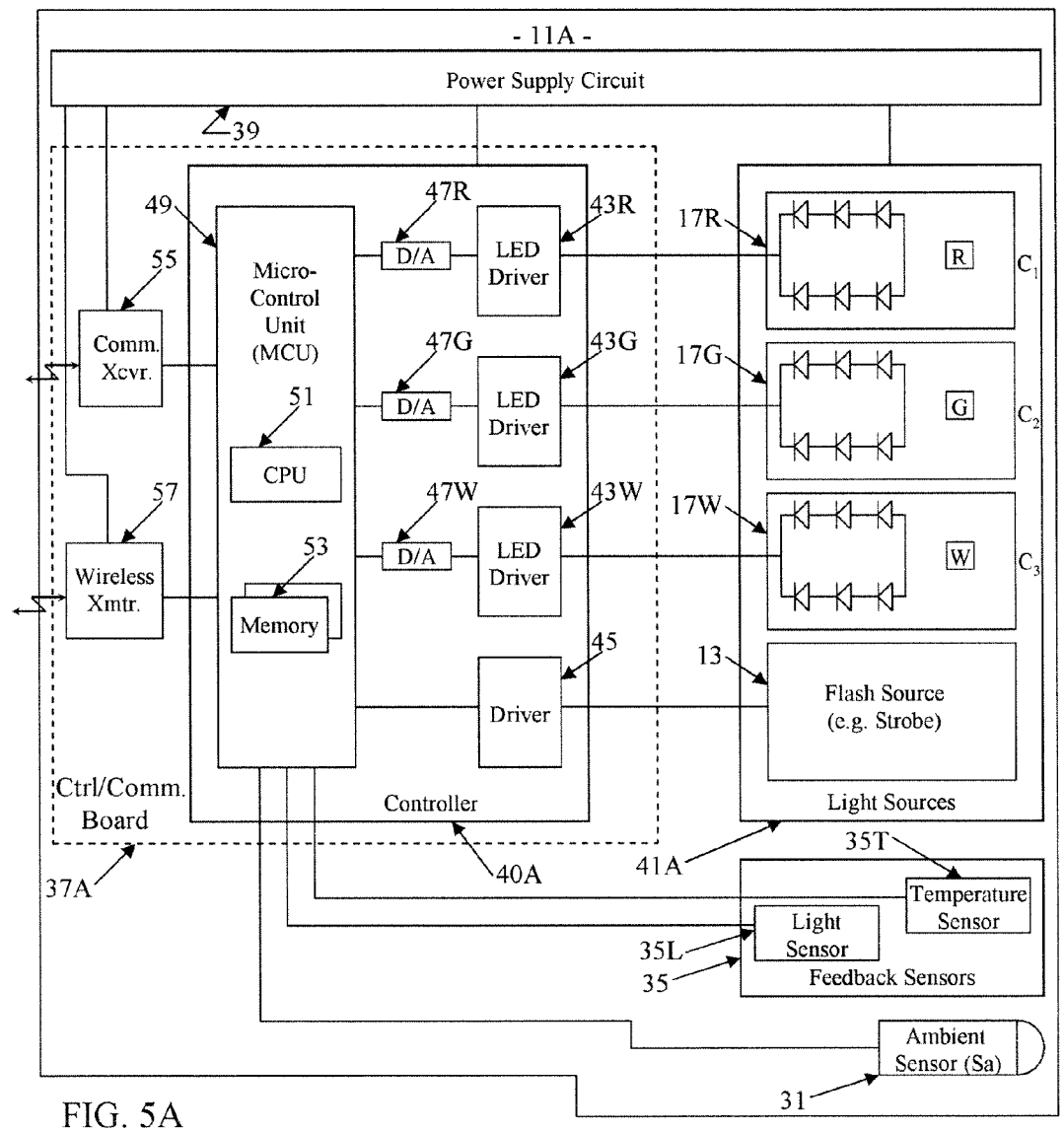
FIG. 5A is a functional block diagram of the electrical elements of the security lighting fixture of FIG. 4A.
Figure 5B:
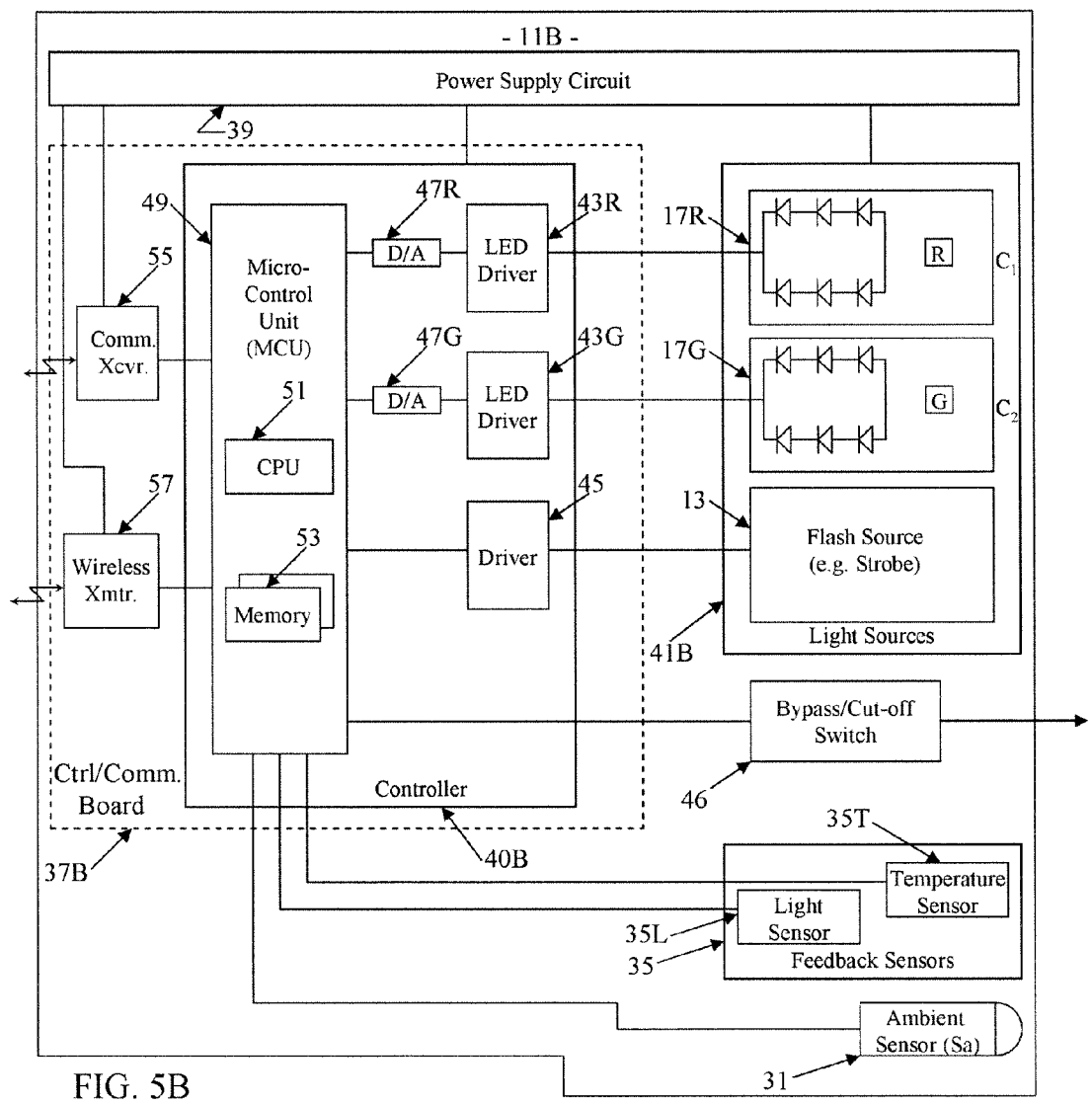
FIG. 5B is a functional block diagram of the electrical elements of the security lighting module of FIG. 4B.

The electrical components shown in the examples of FIGS. 5A and 5B also include a source controller 40A or 40B. In each case, the controller includes drivers corresponding to the particular set of light sources 41A or 41B. Hence, both examples include red and green LED driver circuits 43R, 43G respectively; and both examples include a flash source driver 45 to drive the xenon tube type flash source 13 in our examples. The fixture 11B, which includes white LEDs 17W further includes a corresponding LED driver circuit 43W.

The source controller 40A or 40B also includes a microcontrol unit (MCU) 49. In the examples, the MCU 49 controls the various LED driver circuits 43R, 43G, 43W via respective digital-to-analog (D/A) converters 47R, 47G, 47W. The intensity of the emitted light of a given LED is proportional to the level of current supplied by the respective driver circuit. The current output of each driver circuit is controlled by the higher level logic of the system. The D/A converter 47R controls the driver circuit 43R to provide a drive current to the Red LEDs 17R as specified by the MCU 49, and the D/A converter 47G controls the driver circuit 43G to provide a drive current to the green LEDs 17G as separately specified by the MCU 49. The red and green light outputs, controlled in this way, may be considered as first and second control channels C1 and C2. In a system or fixture, like 11A that includes white LEDs, the D/A converter 47W controls the driver circuit 43W to provide a drive current to the white LEDs 17W as separately specified by the MCU 49; and in such an arrangement, the white light output may considered as another control channel C3. If provided, e.g. for white light or for additional colors or for additional sources of the same or similar light types, other sets of LEDs, forming additional channels, could be controlled/operated in a similar manner.

In operation, one of the D/A converters 47 receives a command for a particular level, from the MCU 49. In response, the converter 47 generates a corresponding analog control signal, which causes the associated LED driver circuit 43 to generate a corresponding power level to drive the particular string of LEDs 17. The LEDs of the string in turn output light of a corresponding intensity. The D/A converter 47 will continue to output the particular MCU specified driver setting level, until the MCU 49 issues a new command to the particular D/A converter 47. Thus, the particular set of LEDs 17 will continue to receive analog current and thus will continue to output light at the set analog level until the MCU 47 changes the applicable setting.

The examples thus implement a form of analog current control for the LEDs, albeit with variations intended to affect visual acuity or perception. Of course, other control strategies may be applied to the LED channels, such as pulse width modulation.

As noted, the MCU 49 controls the xenon tube type flash source 13 in our examples via a flash source driver 45. With a xenon tube type of device, the driver simply triggers the flash in response to a command from the MCU 49. Although other arrangements may allow the MCU to control other parameters of the flash, such as intensity and duration, the examples provide only MCU control over the timing of each flash output.

The MCU 49 in the examples 11A and 11B is a microchip device that incorporates a processor serving as the programmable central processing unit (CPU) 51 of the MCU and thus of the lighting system 11A or 11B. The MCU 49 also includes one or more memories 53 accessible to the CPU 51. The memory or memories 53 store executable programming for the CPU 51 as well as data for processing by or resulting from processing of the CPU 51. The CPU implements the program to process data in the desired manner and thereby generate desired control outputs, for example, to control the other elements of the system 11A or 11B to implement one of the security lighting procedures as discussed herein. The MCU 49 may be structurally the same in both of our representative examples; however, the programming of the MCUs may be different, e.g. to implement different control strategies with respect to the integral white light source provided by the white LEDs 17W and control of other lighting elements for the secured space via the switch 46.

During a security lighting procedure, the respective groups of LEDs are operated alone or in various combinations to produce light emissions in the manner discussed herein. As noted, some LEDs also may be operated alone or in combination at other times to produce white light for normal illumination of the space. Some LEDs may at times be inactive, while other LEDs are operating. Of course, when the security lighting routine is not active and the system is not producing white light for normal illumination, the MCU keeps all LED sources (and the flash source) turned off.

The driver circuits, the A/D converters and the MCU receive power from a power supply 39, which is connected to an appropriate power source (not separately shown). The power supply 39 provides AC to DC conversion if necessary, and converts the voltage and current from the source to the levels needed by various electronic elements on the control and communication (Ctrl./Comm.) board 37A or 37B. For most security lighting applications, the power source will be an AC line current source, however, some applications may utilize DC power from a battery or the like. Also, the security lighting system 11A or 11B may have or connect to a back-up battery or other back-up power source to supply power for some period of time in the event of an interruption of power from the AC mains.

The electrical system associated with the fixture or module, included on the Ctrl/Comm. board 37A or 37B also includes one or more communications interfaces. The examples show two such interfaces, a communication transceiver (Xccvr.) 55 and a wireless transmitter (Xmtr.) 57.

The communication transceiver 55 may be an optical or electrical wired communication device, or the communication transceiver may be an optical or radio frequency type wireless communication device. The transceiver 55 may be a one-way device or a two-way device. For purposes of our discussion, the communication transceiver 55 allows the MCU 49 to communicate with various input and control elements that may be provided in or around the secured space. If the system 11A provides normal lighting in the space, these inputs may include ON/OFF and level (dimming) type control inputs. In both examples, the communication transceiver 55 allows the MCU 49 to receive and detect an input indicative of a breach of security relative to a secured space from one or more elements (not shown) that monitor security. For example, either directly or from logic elements associated with the external security monitoring equipment, the system 11A or 11B may receive inputs regarding the breach of security about activation and/or from devices such an occupancy sensor, an intrusion detector, a code-entry keypad and/or a panic button. The communication transceiver 55 may also allow the system 11A or 11B to communicate with other similar devices in or around the secured space to coordinate security lighting operations of several such systems.

The exemplary devices of FIGS. 5A and 5B also include a wireless transmitter 57. Optical or radio frequency transmitters may be used. In the example, the transmitter 57 is a one-way communication device, although the device could be implemented using a two-way device. The wireless transmitter 57 communicates with shutter goggles, which are configured to mitigate the effects of the security lighting routine. As discussed later relative to FIGS. 8 and 9, the transmitter and goggles allow authorized personnel to respond to and deal with a security breach. If the wireless device 57 is a two-way transceiver, then equipment of the responder, either associated with the goggles or separately operated, could provide an alternate mechanism to indicate that the breach has been cleared and the system 11A or 11B should terminate the security lighting procedure.

As noted in the discussion of FIGS. 4A and 4B above, the electrical components of either system 11A or 11B may also include one or more ambient light sensors (Sa) 31. The sensor Sa 31 provides information regarding ambient lighting, at or before the detecting of the input indicative of the breach of security, as a condition input to the control logic, implemented in this example by the MCU 49. The programming of the CPU 51 configures the MCU 49 to control one or more of the parameters of the security lighting procedure based on the sensed ambient lighting, as outlined earlier.

As further noted in the discussion of FIGS. 4A and 4B above, the electrical components of either system 11A or 11B may also include one or more feedback sensors 35, to provide system performance measurements as feedback signals to the control logic, implemented in this example by the MCU 49. A variety of different sensors may be used, alone or in combination, for different applications.

A temperature sensor 35T, for example, would provide feedback regarding operating temperature of system elements, such as one or more of the LEDs 17. If provided, the temperature sensor 35T may be a simple thermo-electric transducer with an associated analog to digital converter, or a variety of other temperature detectors may be used. The temperature sensor 35T is positioned on or inside of the fixture 11A or module 11B, typically at a point that is near the LEDs or other sources that produce most of the system heat. The temperature sensor 35T provides a signal representing the measured temperature to the MCU 49. The system logic, here implemented by the MCU 49, can adjust intensity of one or more of the sets of LEDs in response to the sensed temperature, for example, to allow the MCU 49 to adjust driver current(s) appropriately so as to achieve programmed LED outputs even though temperatures of the LEDs may vary with time of continuous system operation.

As another example, the system 11A or 11B may include one or more light responsive feedback sensors 35L. Such a sensor 35L, for example, may be positioned to sense light within the cavity 21, or light emitted via the aperture 15 and/or the distal end of the deflector 23. A light sensor 35 may sense intensity and/or a color characteristic of the light produced in or by the system 11A or 11B. Intensity feedback, for example, may be used to adjust drive current to the LEDs. Color characteristic feedback may be used to adjust the drive currents to combinations of LEDs to adjust the characteristic of the integrated LED light output. Feedback from the light sensor 35L may also be used to adjust timing of light emissions and/or a synch signal transmission via the wireless transmitter 53, for example, to help insure synchronization by shutter goggles worn by authorized personnel who may respond to the security breach.

The exemplary systems 11A and 11B of FIGS. 5A and 5B included a number of LED drivers 43 and at least one flash driver 45. A variety of available circuits may be used as these drivers. However, it may be helpful to consider an example of each type of driver.

Figure 6:
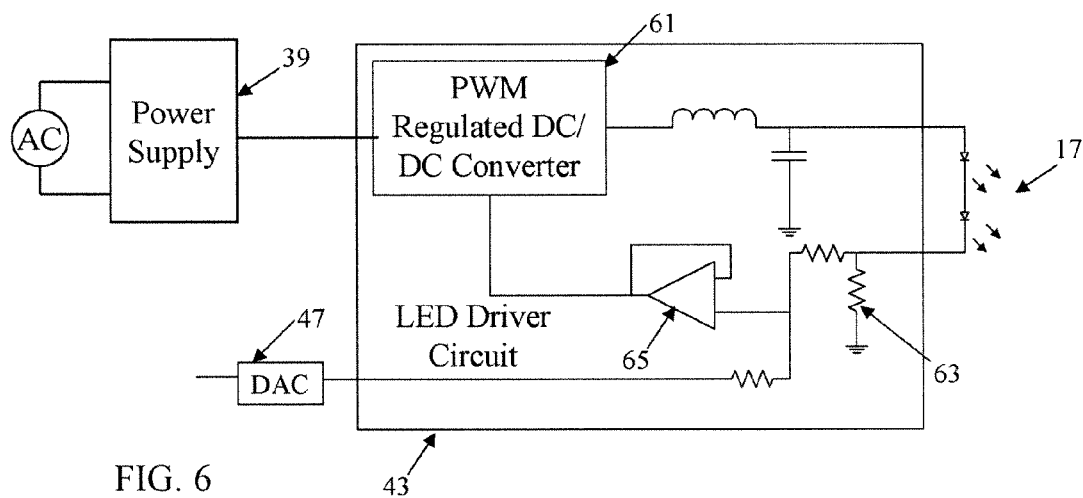
FIG. 6 is a functional block diagram of an LED driver circuit (and associated elements) that may be used in either of the systems of FIGS. 5A and 5B.

FIG. 6 is a functional block diagram of an LED driver circuit 43 that may be used as any of the drivers 43R to 43W in either of the systems of FIGS. 5A and 5B. For discussion purposes, the drawing also shows the associated power supply 39 and the respective digital to analog converter (DAC) 47. The driver circuit 43 employs a switching regulator 61 that uses pulse width modulation (PWM) as its method to convert and regulate a DC voltage/current at its output. The PWM circuit 61, for example, may be a buck or boost converter. The power supply 39 provides a DC voltage to an input of the PWM converter circuit 61. The PWM converter circuit 61 provides a regulated DC voltage/current output, which it supplies through a smoothing circuit (inductor and capacitor in our example) as the drive power to the LEDs 17 in the particular string for the associated control channel.

A digital to analog converter (DAC) 47 is used to set each of the driver circuits in the respective LED control channels to the level of output current required by the LEDs 17 in the associated string in order to achieve the output level specified by the MCU 49. Specifically, the MCU 49 provides a digital output, which the DAC 47 converts to an analog voltage.

There is a current sense resistor 63 in the LED path that provides a feedback voltage for the driver circuit. In the example, the feedback voltage and DAC output voltage are applied as differential inputs to an operational amplifier 65, to produce a control voltage input to the PWM converter circuit 61. For example, if the MCU 49 sends a signal to raise the DC current sent to the LEDs 17 for more brightness, the DAC 47 raises its output voltage accordingly, and the higher voltage setting from the DAC 47 (through the resistor circuit and the amplifier 65) causes the PWM switching regulator 61 of the respective driver 43 to change its operation accordingly. Specifically, the PWM circuit 61 changes the internal PWM duty cycle in order to supply the increased load current until an equilibrium is achieved between the DAC setting and the voltage developed across the feedback resistor 63, at the higher current setting.

Figure 7:
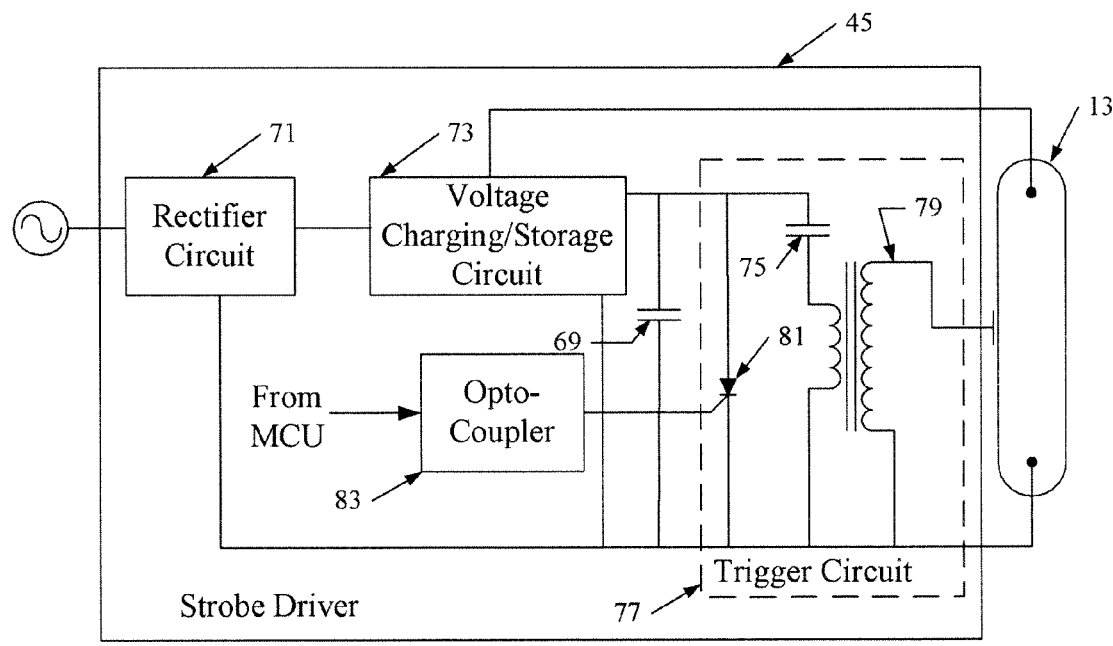
FIG. 7 is a functional block diagram of a strobe driver circuit and a xenon type flash tube, with may be used as the driver and associated flash source in either of the systems of FIGS. 5A and 5B.

FIG. 7 is a functional block diagram of a strobe driver circuit 45 and a xenon tube type flash source 13, which may be used as the driver and associated flash source in either of the systems of FIGS. 5A and 5B. The voltage needed to drive the xenon flash tube type strobe 13 is accumulated on a storage capacitor 69. The driver 45 for the strobe 13 could be configured to draw AC power. In the example, power is applied as alternating current at normal line voltage. The strobe driver circuit 45 includes a rectifier circuit 71, which produces a full wave rectified waveform output to a voltage charging and storage circuit 73. The circuit 73 provides appropriate voltages to the electrodes of the xenon flash tube 13.

The circuit 73 also stores sufficient charge on the capacitor 69 to drive the xenon flash tube 13 and in a capacitor 75 of a trigger circuit 77. The trigger circuit 77 also includes a transformer 79 and a semiconductor switch 81 shown by way of example as a silicon controlled rectifier (SCR). The capacitor 75 is connected to the primary side of the transformer 79. The node formed at the charge inputs to the two capacitors 69, 75 connects to the negative or low voltage side of the circuit through the SCR type switch 81.

The MCU 49 connects to the driver circuit through an optical coupler 83. The optical coupler provides a level of protection between the devices, e.g. to protect the MCU 49 from high voltages/currents or spikes thereof that may be present in the circuit 77 that drives the strobe 13. To trigger a flash, the MCU 49 applies a digital pulse to the input of the optical coupler 83, which causes the output side of the coupler 83 to conduct. The conductivity of the output side of the optical coupler 83 essentially connects the gate of the SCR type switch 81 to the negative or low voltage side of the circuit, for the length of time of the digital pulse signal applied to the coupler 83. This voltage on the gate causes the SCR type switch 81 to conduct. The pulse time of the control input from the MCU 49 controls the time of the cycle of conduction by the switch 81.

When the MCU 49 triggers the SCR type switch 81 to conduct in such a manner, it causes the two capacitors 69 and 75 to discharge, which creates a substantial pulse current flow through the primary winding of the transformer 79. This pulse discharge through the primary winding causes the transformer 79 to generate a high voltage through the secondary winding. The secondary of the transformer 79 is connected to apply that high voltage to the trigger input of the xenon flash tube 13 and causes the tube 13 to flash. After the flash, the xenon tube 13 will stop light emission for some period while the SCR switch 81 is off and the driver circuit 45 recharges. The flash can be fired again in response to a subsequent command pulse from the MCU 49. The programming of the MCU 49 configures the MCU 49 to determine the timing of each such command pulse and thus the time of each triggering of the flash of the xenon tube 13 through the circuit 45.

Figure 8:
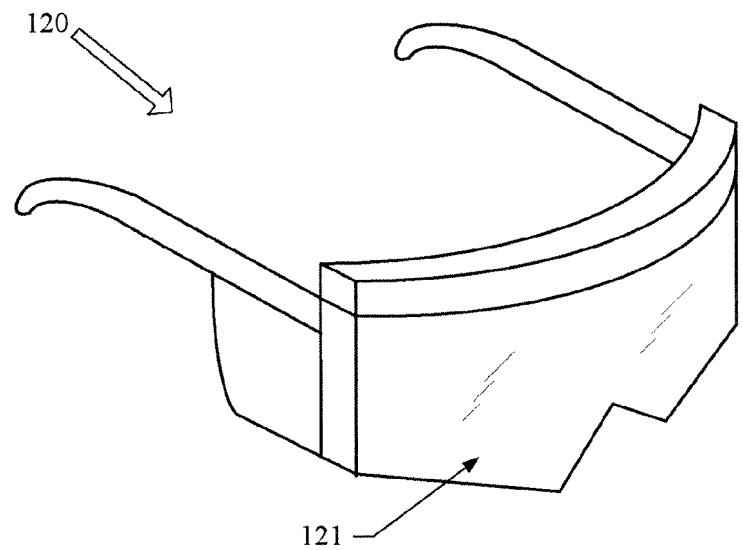
FIG. 8 is somewhat stylized isometric view of a pair of goggles that may be worn by authorized personnel responding to the security breech, configured to reduce the impact of the security lighting algorithm.
Figure 9:
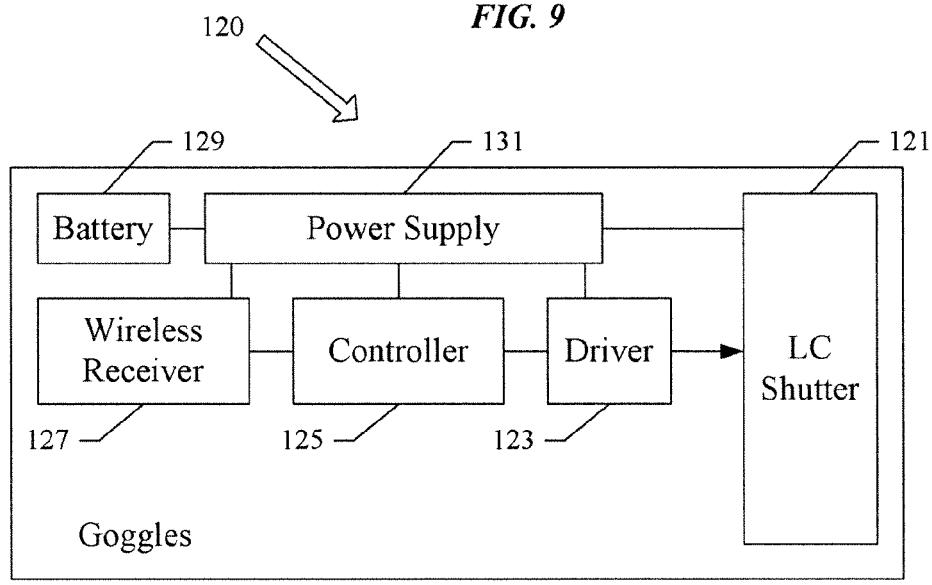
FIG. 9 is a simplified functional block diagram of the elements of the goggles of FIG. 8.

To allow authorized personnel to respond to and deal with a security breach, such a responder can wear shutter goggles, which are configured to mitigate the effects of the security lighting routine. FIG. 8 is an isometric view of an example of a suitable 120 pair of shutter goggles, and FIG. 9 is a functional block diagram of elements of such goggles 120. The form factor shown in FIG. 8 is illustrative only, as other form factors for eyewear or other types of headgear may be used.

The goggles 120 will include a liquid crystal (LC) shutter 121 similar to shutters used in some types of 3D goggles. There may be two shutters, one for each eye. However, the security lighting routine affects both eyes at the same timing and in a similar manner. Hence, the protective shuttering routine implemented by the goggles 120 may be the same for both eyes; therefore the security goggles 120 may have a single LC shutter 121 that is wide enough to work for both eyes, as shown in our example.

An LC shutter such as 120 is an electronic device that tends to be relatively transparent when not driven and thus allows passage of light. However, in response to an appropriate drive signal, the LC panel shifts to a substantially opaque state that blocks passage of light. Pulsing the drive signal effectively causes the LC panel to 'open and close' the electronic shutter in a sequence controlled by the pulses of the drive signal.

For purposes of use with one or more of the security lighting systems 11, the shutter 121 is closed in synchronism with the security lighting algorithm. For example, the shutter 121 will be closed at times to block most if not all of each of the high intensity flashes. To reduce the disorientation during the multi-color lighting sequence, the shutter 121 may also close at times to block all but one of the different colors of light pulses. However, the electronic shutter 121 will be open for some portion of light emission to allow the wearer of the goggles to function in the space during the security lighting operations. For example, the shutter 121 of the goggles 120 may pass light during any dim illumination and pass emissions of one color during the multi-color sequence. The unblocked single color emission from the sequence would appear to the wearer as a pulsing single color light.

As shown in the block diagram of FIG. 9, the security goggles include the LC shutter 121 and a driver circuit 123 for providing the pulse drive signal to the LC shutter 121. The goggles also include a controller 125 for activating the driver 123 at the appropriate timing and for respective durations. The controller 125, for example, may be a programmed micro-controller or a suitable logic circuit.

The security goggles also include a wireless receiver 127. The wireless receiver may be a radio device such as an RF receiver, an optical device such as an infrared receiver, or other suitable device.

The wireless receiver 127 and the controller 125 are configured to receive an encoded wireless signal from a particular security lighting system 11. Various encoding/decoding schemes may be used. Of note for purposes of discussion here, the security lighting system(s) 11 in a particular installation emit a signal encoded in a manner that requires a unique key or code in order to decode properly. Only one or some small number of pairs of goggles 120, intended for authorized personnel for the particular installation, will be programmed with the particular key or code.

The controller 125 is programmed or otherwise configured to recover a synchronism signal associated with the security lighting algorithm. In response, the controller 125 activates the driver 123 and thus the LC shutter 121 in synchronism with emissions from the security lighting system(s) 11, as outlined earlier.

The goggles will include or connect to a portable power source, such as one or more batteries 129 shown in FIG. 9. Any suitable battery may be used. A power supply circuit 131 converts the battery power to the voltage and/or current levels required by the receiver 127, the controller 125, the driver 123 and the LC shutter 121.

Alternatively, the goggles could close the shutter to block the flash, but could incorporate an appropriate optical notch or band-stop filter to block one of the two different color light components while passing the other. Assuming an R-G sequence for example, the goggles might incorporate a red-pass filter that blocks at least a substantial amount of the green portion of the visible spectrum (including the narrow wavelength of emissions of the green source).

Figure 10:
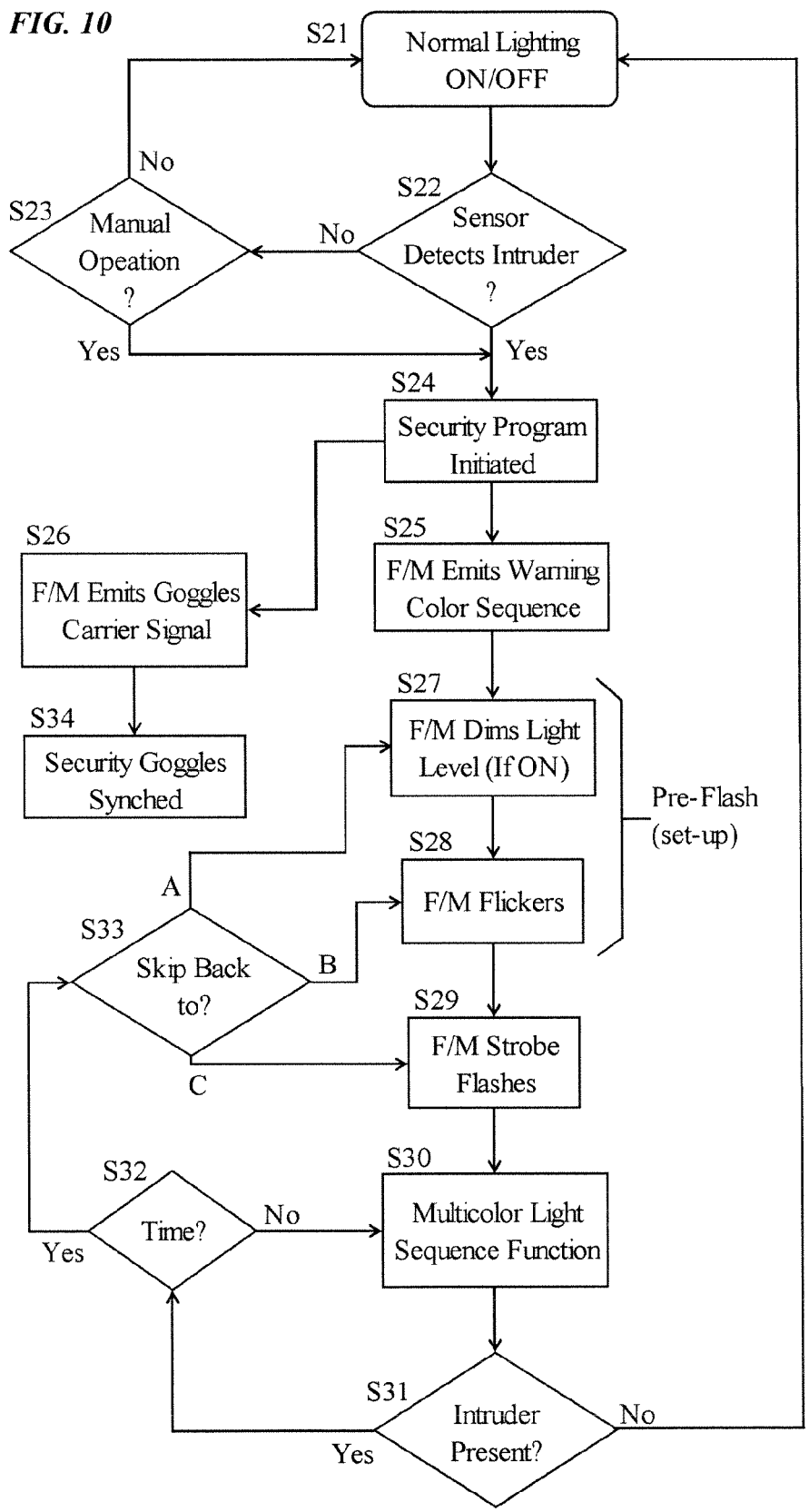
FIG. 10 is a flow chart of a more detailed example of a security lighting procedure as may be implemented using one or more of the devices of FIGS. 3-4B.

FIG. 10 is flow chart of a further example of a security lighting procedure, which combines many aspects of various procedures outlined above into one overall lighting routine. For example, the procedure of FIG. 10 may be implemented by any of the security lighting systems mentioned earlier, such as the fixture 11A or the module 11B. For convenience, several steps refer to the fixture/module alternative implementations as "F/M." The order of the steps are given by way of example, and some or all of the steps may be omitted or may be implemented in an order different from that illustrated in the drawing.

As shown at step S21, lighting in the secured space is operating in a normal manner and may be either ON (full or dimmed) or OFF. As noted in earlier discussions, a fixture implementation using one or more instances of the fixture 11A may provide the normal illumination; or if a security module 11B is used, normal illumination would be provided by other lighting elements, although the module 11B would be able to control at least some aspect(s) of operation of any such other lighting elements during the security lighting procedure.

The illustrated procedure includes a loop through steps S22 and S23 and back to S21 in which the system determines if there is a security breach, and if not, continues normal lighting operations in the secured space. There may be a variety of types of detections/decisions used to determine whether or not there has been a security breach, some automatic and some manual, as outlined above. The example assumes that the system receives inputs regarding whether or not there has been a security breach via communications with at least one sensor for automatic detection and at least one switch or other trigger device for manual activation. Hence, in the example of FIG. 10, the procedure includes a branch or decision step at S22 in which the system determines if it has received an indication of a breach from the sensor, that is to say, whether or not the sensor has detected an intruder in this example. If not, the processing flows to step S23 in which the system determines if it has received an indication of a breach from the manual input device, that is to say, whether or not there has been a manual operation to activate the security lighting emission program. If not, the processing flows back to step S21 in which the system continues the normal ON or OFF state of the lighting of the secured space. In either or steps S22 and S23, if the security lighting system receives an indication of a breach of security from either the sensor (in S22) or the manual input device (in S23), then processing branches from the respective step to step S24, in which the system initiates execution of its security lighting emission program.

At step S24, the security lighting system, i.e. the fixture or module (F/M) used for the particular secured space, initially triggers a warning light emission. Although the detection and return path is omitted, for ease of illustration, if the breach is cleared during the period of the warning light emission, processing would branch back to normal lighting in step S21. The warning light may be a low and/or flashing emission of a pre-set warning color of light, e.g. red light. The parameters of the warning light emission typically would attract some attention and provide the desired warning but need not be tailored to disrupt visual perception and/or acuity.

Initiation of the security lighting program at step S24 also initiates transmission of a wireless signal to synchronize shutter operations of any goggles to be worn by authorized responders. Hence, at step S26 the wireless transmitter 57 of the fixture or module (F/M) used for the particular secured space emits a carrier signal that is encoded and includes a synch signal corresponding to the lighting emissions that will be implemented by the fixture or module during the activated security light emission procedure. When initially activated, however, the responders likely will not have reached the secured space and/or authorized personnel in the space may not yet have donned security goggles. Hence, our discussion here will follow the light emissions steps.

Assume for the moment, that when the step S22 or S23 indicates that there has been a breach of security, the lighting at step S21 has previously been ON (full or somewhat dimmed). In such a case, in the example of FIG. 10, if the breach of security is not cleared by a predetermined time of warning light emission, the fixture or module (F/M) will dimly light the secured space at an intensity sufficiently lower than the normal full intensity level for the space and for a sufficient period to cause pupils of a person in the space to dilate (step S27). Dim lighting may be white light or any colored light. The level of the dim lighting may be approximately 50% or less that the normal full intensity level for the space and may persist for some number of seconds.

The dim lighting step S27, however, may be skipped if in the step S21 before the security breach detection at S22 or S23 the normal lighting was sufficiently dim or OFF. Also, if the normal lighting was sufficiently dim or OFF before the detection of the security breach, then intensity of the warning light emission in the step S25 would be kept sufficiently low so as to minimize or avoid causing a persons pupils to substantially close due to the warning light emission.

In any of these process flows through S25 and S27, when the process flow reaches step S28, lighting has been dim for a substantial enough period to insure dilation. As a result, the pupils of anyone within the secured space at that time should be relatively wide open. At step S28, the fixture or module (F/M) emits a short flicker of light into the secured space. Flicker may be somewhat brighter, around or even lower in intensity than the level of dim lighting. Since the exemplary procedure of FIG. 10 involves dim lighting before the flicker, either in the warning emission (S25) or the dim light emission (S7) depending on the prior state of normal lighting in the space, the flicker emission may be in a range of 10 to 50% of the normal full intensity level for the secured space. The flicker typically comprises some small number of flashes separated by periods of no or low light emission, over a relatively short time period, such as 2 or 3 flashes within a second or less. The pulse frequency is below a human's optical fusion rate so as to be perceived as flicker rather than as a continuous light emission. The flicker typically is white but may be red or some other color of light.

In the example of FIG. 10, the steps S27 and S28 provide the pre-flash light emission to set-up any person(s) in the secured space, so as to improve effectiveness of the flash emission. Hence, following the flicker in step S28, the fixture or module (F/M) activates the flash source 13 in step S29. In our specific system examples (FIGS. 3-5B), the xenon strobe 13 flashes. The flash emission will have an intensity level at least twice the normal full intensity level for the space. As noted earlier, the flash intensity may be several times the normal full intensity level; or the flash intensity level may be one, two or more orders of magnitude greater than the normal full intensity level. With the target set-up to maximize the impact of the flash on the subject(s) within the space, the bright flash in step S29 tends to cause temporary flash blindness and/or a persistent after image as discussed with respect to earlier examples.

After the flash, the fixture or module (F/M) operates the multiple color light sources, various LEDs 17 in our examples, to produce a multi-color light sequence emission function in step S30. The emission function in step S30 in this example will produce a repeated sequence of: (1) emitting a first color of light, (2) emitting no light following the emission of light of the first color, (3) emitting a second color of light different from the first color of light, and (4) emitting no light following the emission of light of the second color of light. As discussed later in part of the discussion of FIG. 11, there may be additional colors of light emission in step S30. The fixture or module (F/M) will vary parameters of the sequence and its repetitions in an irregular manner. For example, in the sequence emission/repetitions in step S30, two or more parameters of the emission of light of the first color differ from the two or more parameters of the emission of light of the second color of light, within each repetition of the sequence and/or among successive repetitions of the sequence. Also, the lengths of the emissions of no light after the emissions of light of the first and second colors may differ, within each repetition of the sequence and/or between different repetitions of the sequence within step S30.

In our example, each "color" in the sequence is a light of a relatively narrow wavelength band, e.g. as might be produced by a substantially mono-chromatic light source such as an LED of a particular color. The pulse on times, pulse off times, pulse frequencies and/or overall sequence repetition frequency are such that a human will clearly see the different light colors and will often be able to see the off times. As such, the multi-color sequence emissions are configured such that any apparent repetition rate is below a human's visual fusion frequency (the lower frequency at which the human nervous system tends to integrate light variations into a continuous image). However, the sequence and repetitions thereof, with the two or more different colors of light emissions and the parameter variations, are configured so that the multi-color light sequence emission tends to further disrupt visual perception and/or acuity and thereby may temporarily disorient or disable any person within the space at least to the extent necessary to reduce the likelihood of their achieving their nefarious purpose in breaching security of the space in which they have intruded.

In the exemplary procedure of FIG. 10, the sequence of multiple color light emissions (step S30) will continue for some period of time unless the breach has been cleared. Hence, the process includes a decision step S31 in which the security lighting system determines whether or not the intruder is still present. Examples of just a few ways that the breach clearance determination might be made, based on a manual input and/or an automatic detection status from an intrusion detector or other sensor have been outlined above. In the process flow of FIG. 10, at step S31 if the intruder is no longer present (security breach cleared) the process flow branches back to the initial lighting and monitoring loop (S21 to S23). The process could return to S22 or S23, but in the example, the process branches back to normal lighting at step S21. Lighting in the space will return to normal, e.g. to a normal full ON state or possibly to another state of the lighting prior to the breach.

However, when the process flow is at step S31, but the intruder is still present (security breach not yet cleared), then the process flow branches to step S32. The high level logic, e.g. the MCU, of the security lighting fixture or module (F/M) maintains a timer that is used to determine a time that the multi-color light sequence emission function should operate while the security breach has not been cleared. Any convenient or efficient timing procedure may be used. If the time limit has not been reached, the process flow branches from step S32 back to step S30 and the multi-color light sequence emission function continues. In this way, if the intruder remains present, then processing will loop through steps S30-S32 until the time limit is reached. At S32, when the MCU or other high level logic of the security lighting fixture or module (F/M) determines that the time of the multi-color light sequence emission function has reached the limit, the process flow branches from S32 to step S33.

The time limit used in step S32 could be a fixed parameter. However, to increase variability of the overall procedure of FIG. 10, the time limit used in step S32 would be a variable parameter. Each time that the process flow reaches the multiple color light emissions in step S30 from the flash step S29, high level logic of the security lighting fixture or module (F/M) would select a different time limit. In this manner, an intruder in the secured space would not be able to adjust to the time period of the multiple color light emissions in step S30 even after several iterations of that step.

As noted in the discussion of steps S5 and S7 of FIG. 1, the processing after the multi-color light sequence emission may branch back to one of the earlier steps of the process flow. In the exemplary procedure of FIG. 10, rather than being a fixed branch back to one particular earlier step, the procedure includes a variable decision step. Hence, at step S33, when the time limit is reached, the logic of the security lighting fixture or module (F/M) selects one of several of the earlier steps of the procedure to which to skip back. By way of example, the skip back selection step S33 involves a selection among three of the earlier steps, and processing branches back to the selected earlier step. Of course, the selection could be among two earlier steps or among some higher number of earlier steps. The earlier steps for the skip, in our example, are the dim lighting step S27 (via branch A), the flicker step S28 (via branch B) and the flash step S29 (via branch C). The selection of the branch at step S33 can be irregular, e.g. random, chaotic or biological, in order to further reduce the ability of an intruder to adjust to parameters of the process flow.

Depending on the return path selected each time at step S33, the security lighting fixture or module (F/M) will repeat the flash (S29), repeat the flicker (S28) and the flash (S29) or repeat the dim lighting (S27), the flicker (S28) and the flash (S29). After the repeat of the flash, processing again reaches the multiple color light emissions in step S30, which will run for the time set by the current limit of step S32, unless the breach is cleared as detected in step S31. Hence, the selective skip back step S33 connects the steps together to form an extended repetitive loop through variable combinations of steps S27 to S33, which will enable the security lighting fixture or module (F/M) to produce various light emission as outlined above but in various orders and with various control parameters until the breach of the security is cleared.

As noted earlier, initiation of the security lighting program at step S24 also initiates transmission of a wireless signal to synchronize shutter operations of any goggles to be worn by authorized responders, as represented by step S26 in the flow chart. After some period of operation of the security lighting program (e.g. steps S25 through S33), a responder may arrive to deal with the security breach. Assuming that the security lighting operations have been effective, the intruder(s) that may still be in the secured space will have disrupted visual perception and/or acuity and thus diminished visual capacities. A responder will be wearing a set of the security goggles, an example of which has been discussed above relative to FIGS. 8 and 9. At step S34 in the process flow, the wireless receiver 127 in the goggles 120 will receive the carrier signal, the receiver 127 and/or the controller 125 will decode the wireless signal and recover the synchronizing signal sent by the transmitter 57 of the security lighting fixture or module (F/M) in step S26. Based on the recovered synchronizing signal, the controller 125 in the goggles 120 activates the driver 123 and thus the LC shutter 121 in synchronism with emissions from the security lighting system. The appropriately timed closing of the shutter in the goggles will reduce or eliminate the impact of the light emissions on the eyes of the responder sufficiently so as to allow the responder to function appropriately upon reaching the secured space, even while the security lighting procedure continues to cycle through the various light emissions. Hence, the intruder's ability to function is likely diminished but the responder's ability to function likely is not diminished, enhancing the responder's ability to appropriately deal with the intruder.

Figure 11:
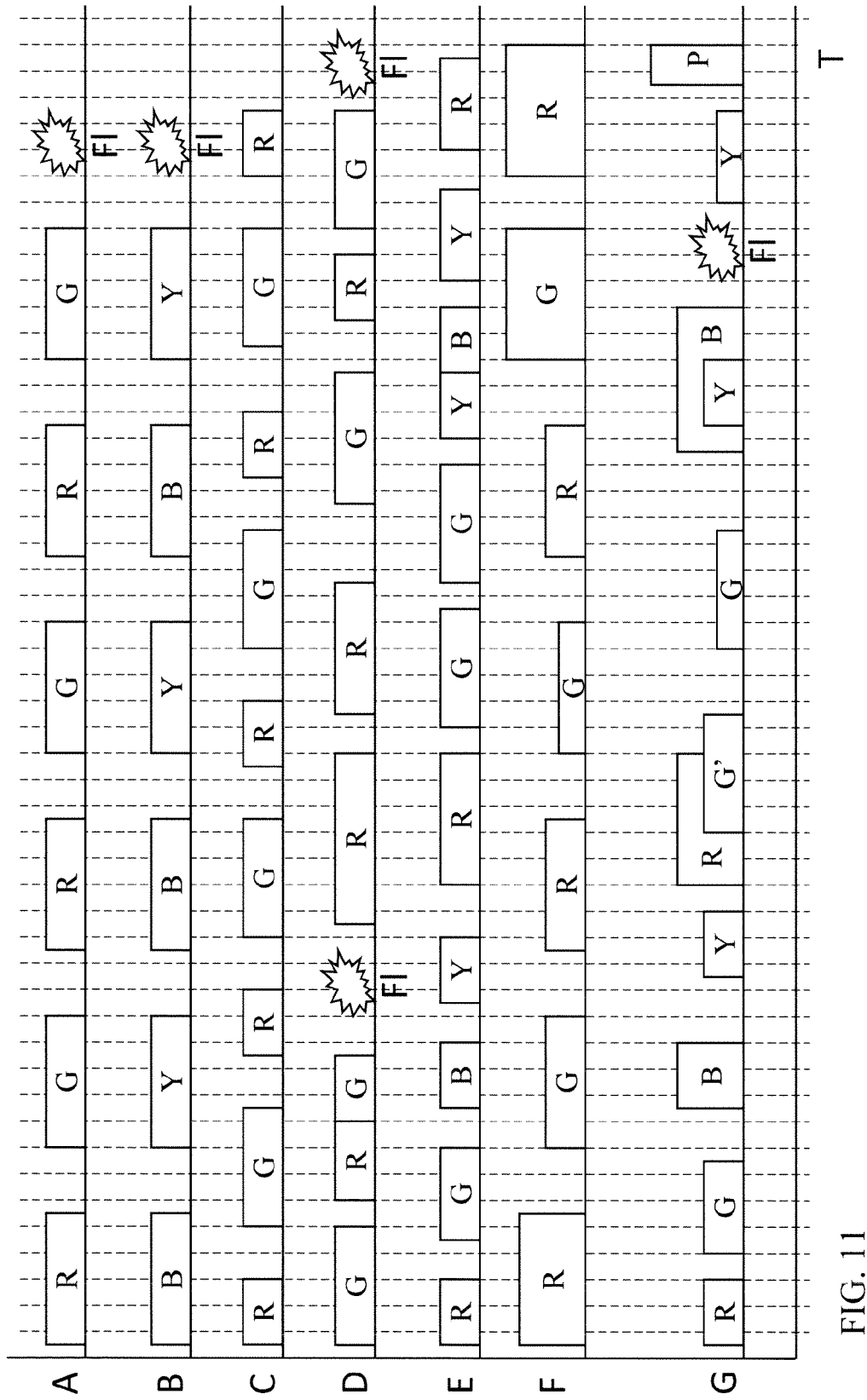
FIG. 11 is a more detailed pulse diagram regarding the sequence in a multi-color light sequence emission step, in one of the exemplary security lighting procedures.

FIG. 11 is a pulse diagram that may be helpful in understanding many of the parameters and variances in parameters of a security lighting procedure. Although the warning light, dimming and flicker emissions are not shown, for ease of illustration, the diagram of FIG. 11 depicts emissions of the other emitting steps of a process like that of FIG. 1 or FIG. 10.

The overall security lighting sequence can utilize any number of different emission variable parameters. Examples of such variables include spectral content (color). To that end, the system may emits primary colors, such as Red (e.g. dominant wavelength 610 nm), Green (e.g. dominant wavelength 530 nm), (yellow and blue in several examples, black (no light) and flash (Strobe Flash). Secondary colors also may be used, such as Blue (e.g. dominant wavelength 480 nm) and Yellow (e.g. dominant wavelength 570 nm); any other tertiary color of light may be added if either deemed useful in disruptive effects or deemed useful in assisting a wearer of the security goggles (without diminishing disruptive effects on the intruder). Other types of variable parameters includes Pulse Length (length of the optical pulse of a specific color or flash), Amplitude (intensity of the optical pulse of a specific color or flash), Duty Cycle (% "on" time of the pulse(s)), Temporal Frequency (length of a repeating pattern, if any), and the like.

The operations of light emissions in a security lighting procedure could operate in a controlled pattern, e.g. to produce a predetermined, programmed, and repeatable output sequence. However, to improve effectiveness particularly on different individuals of different characteristics, the systems discussed herein typically vary one or more parameters of the security lighting emissions in an irregular manner. The irregular variations may be somewhat random, such that values of the output sequence are created by chance. Another approach involves controlling variation(s) of the operation parameter(s) based on a chaotic function, e.g. based on three linked differential equations at the transition point from orderly to disorderly. Still another approach involves controlling variation(s) of the operation parameter(s) based on a biological function. With this later approach, an output sequence is intended to couple to a known biological function, such as temporal frequency in light level adaptation of humans. Also, it is possible to use any combination of these parameter control strategies, e.g. superimposed or sequenced in relation to one another. Of course, other control strategies may be adopted in order to optimize effectiveness of the security lighting sequence.

Consider now the various examples represented by the pulses in the various lines in FIG. 11.

Line A of FIG. 11 shows a two color pulse sequence followed by a return to the flash. The illustrated sequence is configured to provide fixed: spectral content (always the same two different colors together with the white flash), pulse length, amplitude, duty cycle and temporal frequency of each primary color (red, green or white flash) emission. Line B shows a security lighting emission pattern or sequence similar to that of Line A, but in which different colors have been substituted. In the example of Line A, the colors in the multi-colored light emission part of the sequence are red (R) and green (G), whereas in the example of Line B, the colors in the multi-colored light emission part of the sequence are blue (B) and yellow (Y).

Line C of FIG. 11 shows a two color pulse sequence, using the same colors as Line A, although obviously other colors could be used. The example of Line C is configured to provide fixed spectral content and fixed pulse amplitude. However, in that third example, the different colors have non-equal duty cycles/pulse lengths. Although the off times between pulses and/or the frequencies of the pulses of each color may vary as well, in this example, just the ON-time of the pulse duty cycles vary.

Line D depicts an example of a sequence of multiple color emissions and flash emissions. That example shows variation of pulse length, duty cycle and temporal frequency (including 0 off time between at least two pulses). For purposes of illustration, the example in Line D utilizes the red (R) and green (G) and has spectral content similar to lines A and B, although obviously other colors could be used. Line E represents a security lighting sequence that is generally similar to that of Line D, except that the sequence in Line E includes secondary colors, blue (B) and yellow (Y) in the illustrated example.

Line F of FIG. 11 shows an example of a two color pulse sequence with variable duty cycles similar to Line C. However, in Line F, the amplitude of light emission also varies from pulse to pulse in the sequence. Hence, in the exemplary sequence of Line F, two parameters (amplitude and pulse on length of duty cycle) of the emission of light of the first color (R) vary pulse to pulse within the illustrated complete repetition of the sequence (the complete line); and the two parameters (amplitude and pulse on length of duty cycle) of the emission of light of the second color (G) vary pulse to pulse within the illustrated complete repetition of the sequence (the complete line). The same parameters would also vary from repetition to repetition. Although not separately shown, several repetitions of a sequence like that of Line F would typically be preceded by a flash and followed by one or more light emission steps that would include a flash.

Line G of FIG. 11 shows an example of a pulse sequence with variations of two parameters (amplitude and pulse on length of duty cycle) of the emission of light. Line G, however, represents an addition of overlapping light pulses and of different tertiary colors and/or hues.

The light emissions, like those in the examples in the various lines in FIG. 11, can be combined or subtracted in any form. There are an infinite number of combinations and permutations that are possible. The purpose of building this set of examples was intended to show how the complexity of the output can grow, as well as how all of the individual variables can be manipulated. It is by no means complete and should not be viewed as limiting.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," "includes," "including," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

Unless otherwise stated, any and all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

What is claimed is:

1. A method, comprising steps of:
   (a) detecting an input indicative of a breach of security relative to a space that is normally illuminated at an intensity level normal for human occupancy of the space;
   (b) emitting a set-up light into the space, the set-up light having an optical characteristic to set-up eyes of a person within the space to be susceptible to subsequent bright lighting; and
   (c) following the set-up light emission, emitting a light in an irregular manner to disrupt visual perception or acuity and temporarily disorient or disable any person within the space, wherein:
   the step of emitting the light in an irregular manner comprises repeatedly in sequence (1) emitting a first color of light, (2) then emitting no light of at least the first color of light, (3) emitting a second color of light different from the first color of light, and then (4) emitting no light of at least the second color of light; and
   a plurality of operational parameters of the emissions of the sequence vary within each repetition of the sequence and differ between successive repetitions of the sequence in an irregular manner.

2. The method of claim 1, wherein the step of emitting the light in an irregular manner comprises first emitting a flash of light at an intensity level at least twice the normal intensity level for the space.

3. The method of claim 1, wherein:
   the step of emitting the set-up light comprises dimly lighting the space at an intensity sufficiently lower than the normal intensity level for the space and for a sufficient period to cause pupils of a person in the space to dilate.

4. The method of claim 3, wherein the step of emitting the set-up light further comprises, following the dim lighting, emitting a short flicker of light into the space.

5. The method of claim 1, wherein:
   the step of emitting the set-up light comprises emitting a short flicker of light into the space.

6. A security lighting system, comprising:
   a first colored light source, configured to emit light of a first color;
   a second colored light source, configured to emit light of a second color different from the first color;
   another light source, configured to emit light at an intensity lower than a normal full intensity level for a space;
   a controller, which has an input for receiving an indication of a breach of security, and is coupled to control operations of the light sources;
   wherein the controller is configured to control operations of the system to impellent security lighting functions, including functions to:
   (a) receive an input indicative of a breach of security relative to a space that is normally illuminated at an intensity level normal for human occupancy of the space;
   (b) emit, by the another light source, a set-up light into the space, the set-up light having an optical characteristic to set-up eyes of a person within the space to be susceptible to subsequent bright lighting; and
   (c) following the set-up light emission, emit, by the first and second colored light sources, a light in an irregular manner to disrupt visual perception or acuity and temporarily disorient or disable any person within the space.

7. The system of claim 6, wherein the function to emit the set-up light comprises a function to dimly light the space at an intensity sufficiently lower than the normal intensity level for the space and for a sufficient period to cause pupils of a person in the space to dilate.

8. The system of claim 7, wherein the function to emit the set-up light further comprises a function to, following the dim lighting, emit a short flicker of light into the space.

9. The system of claim 8, further comprising a strobe light configured to emit a bright flash of light wherein the implemented function to emit the light in an irregular manner further comprises a function to emit, prior to emitting the light in an irregular manner and by the strobe light, a flash of light at an intensity level at least twice the normal intensity level for the space.

10. The system of claim 6, wherein the function to emit the set-up light comprises a function to emit a short flicker of light into the space.

11. The system of claim 10, further comprising a strobe light configured to emit a bright flash of light wherein the implemented function to emit the light in an irregular manner further comprises a function to emit, prior to emitting the light in an irregular manner and by the strobe light, a flash of light at an intensity level at least twice the normal intensity level for the space.

12. The system of claim 6, wherein:
   the implemented function to emit the light in an irregular manner comprises a function to repeatedly in sequence (1) emit, by the first colored light source, the light of the first color, (2) then emit no light of at least the first color, (3) emit, by the second colored light source, the light of the second color, and then (4) emit no light of at least the second color; and
   a plurality of operational parameters of the emissions of the sequence vary within each repetition of the sequence and differ between successive repetitions of the sequence in an irregular manner.

13. The system of claim 12, further comprising a strobe light configured to emit a bright flash of light wherein the implemented function to emit the light in an irregular manner further comprises a function to emit, prior to emitting the light in an irregular manner and by the strobe light, a flash of light at an intensity level at least twice the normal intensity level of the space.

14. A security lighting system, comprising:
   at least one light source configured to emit light; and
   a controller, which has an input for receiving an indication of a breach of security, and is coupled to control operations of the at least one light source;
   wherein the controller is configured to control operations of the system to impellent security lighting functions, including functions to:
   (a) detect an input indicative of a breach of security relative to a space that is normally illuminated at an intensity level normal for human occupancy of the space;
   (b) emit a set-up light into the space, the set-up light having an optical characteristic to set-up eyes of a person within the space to be susceptible to subsequent bright lighting; and
   (c) following the set-up light emission, emit a light in an irregular manner to disrupt visual perception or acuity and temporarily disorient or disable any person within the space, wherein:

the function to emit the light in an irregular manner comprises repeatedly in sequence (1) emitting a first color of light, (2) then emitting no light of at least the first color of light, (3) emitting a second color of light different from the first color of light, and then (4) emitting no light of at least the second color of light; and a plurality of operational parameters of the emissions of the sequence vary within each repetition of the sequence and differ between successive repetitions of the sequence in an irregular manner.

\* \* \* \* \*